(12) United States Patent
Matsumura et al.

(10) Patent No.: US 11,812,739 B2
(45) Date of Patent: Nov. 14, 2023

(54) VITREOUS STATE STABILIZING AGENT FOR ANIMAL CELL CRYOPRESERVATION SOLUTION

(71) Applicant: JAPAN ADVANCED INSTITUTE OF SCIENCE AND TECHNOLOGY, Nomi (JP)

(72) Inventors: Kazuaki Matsumura, Nomi (JP); Toshiaki Naka, Kanazawa (JP)

(73) Assignee: JAPAN ADVANCED INSTITUTE OF SCIENCE AND TECHNOLOGY, Ishikawa (JP)

( * ) Notice: Subject to any disclaimer, the term of this patent is extended or adjusted under 35 U.S.C. 154(b) by 693 days.

(21) Appl. No.: 16/077,801

(22) PCT Filed: Feb. 15, 2017

(86) PCT No.: PCT/JP2017/005592
§ 371 (c)(1),
(2) Date: Aug. 14, 2018

(87) PCT Pub. No.: WO2017/141991
PCT Pub. Date: Aug. 24, 2017

(65) Prior Publication Data
US 2021/0084891 A1    Mar. 25, 2021

(30) Foreign Application Priority Data
Feb. 17, 2016  (JP) .................................. 2016-027612

(51) Int. Cl.
*A01N 1/02*    (2006.01)

(52) U.S. Cl.
CPC .................................. *A01N 1/0221* (2013.01)

(58) Field of Classification Search
CPC ........... A01N 1/02; A01N 1/0221; C12N 1/04
See application file for complete search history.

(56) References Cited

U.S. PATENT DOCUMENTS

| | | | |
|---|---|---|---|
| 3,300,474 A | 1/1967 | Flodin et al. | |
| 9,826,732 B2 | 11/2017 | Matsumara et al. | |
| 2006/0134596 A1* | 6/2006 | Sjogren | A61K 35/54 435/2 |
| 2011/0172315 A1 | 7/2011 | Matsumara et al. | |
| 2018/0160676 A1 | 6/2018 | Matsumara et al. | |

FOREIGN PATENT DOCUMENTS

| | | |
|---|---|---|
| JP | 2000-500327 | 1/2000 |
| JP | 2011-30557 A | 2/2011 |
| JP | 2011-36196 A | 2/2011 |
| JP | 2012-217342 A | 11/2012 |
| JP | 5630979 | 11/2014 |
| JP | 5630979 B2 | 11/2014 |
| JP | 2016-220672 A | 12/2016 |
| WO | 97/14785 | 4/1997 |
| WO | 2009/157209 A1 | 12/2009 |

OTHER PUBLICATIONS

Sigma webpage https://www.sigmaaldrich.com/technical-documents/protocols/biology/ficoll-400.html (2021) downloaded Apr. 27, 2021 (Year: 2021).*
Machine translation of JP 2011030557A published Feb. 17, 2011, downloaded from the EPO on Apr. 27, 2021 (Year: 2011).*
International Search Report dated May 9, 2017, issued in counterpart application No. PCT/JP2017/005592. (2 pages).
Suzuki et al., "Sosuika Ryosei Denkaishitsu Kobunshi no Toketsu Hogo Koka", Dai 37 Kai The Annual Meeting of the Japanese Society for Biomaterials Yokoshu, Nov. 2015, p. 284, 2P-011, cited in ISR. (3 pages).
Suzuki et al., "Shinki Glass-ka Jotai Anteika Kobunshi no Kaihatsu", Dai 60 Kai Japanese Society for Cryobiology and Cryotechnology Seminar Oyobi Nenkai Koen Yoshishu, May 2015, p. 19, B11, cited in ISR. (3 pages).
Notification of Transmittal of Translation of the International Preliminary Report on Patentabililty (Form PCT/IB/338) issued in counterpart International Application No. PCT/JP2017/005592 dated Aug. 30, 2018 with Forms PCT/IB/373 and PCT/ISA/237. (8 pages).
Suzuki, M. et al., "Cryoprotective Effect of Hydrophobic Ampholitic Polymers", Proceedings of the 37th Annual Meeting of the Japanese Society for Biomaterials, Nov. 2015, p. 284, 2P-011. (2 pages) (English translation of document filed on Aug. 14, 2018).
Suzuki, M. et al., "Development of a Novel Polymer in a Stabilized Vitrified State", Lecture abstracts of the 60th Seminar and Annual Meeting of the Japanese Society for Cryobiology and Cryotechnology, May 2015, p. 19, B11. (2 pages) (English Translation of document filed on Aug. 14, 2018).
International Search Report dated Oct. 18, 2016 in corresponding PCT Application No. PCT/JP2016/071169.
Written Opinion of the International Searching Authority dated Oct. 18, 2016 in corresponding PCT Application No. PCT/JP2016/071169.
Kazuaki Matsumura, "Development of polymer cryoprotectants and their biomedical applications", The 36th Annual Meeting of the Japanese Society for Biomaterials Yokoshu, 2014 Nen 11 Gatsu, p. 166, with English Translation.

(Continued)

*Primary Examiner* — Nghi V Nguyen
(74) *Attorney, Agent, or Firm* — GREENBLUM & BERNSTEIN, P.L.C.

(57) ABSTRACT

Provided are a vitrification stabilizer for an animal cell cryopreservation fluid, and an animal cell cryopreservation fluid which exhibits superior vitrification capabilities due to the animal cell cryopreservation fluid containing the vitrification stabilizer for an animal cell cryopreservation fluid. The vitrification stabilizer for an animal cell cryopreservation fluid contains: an amphoteric polymer compound selected from the group consisting of (a) a carboxylated amphoteric polymer compound obtained by reacting ε-poly-L-lysine with butyl succinic anhydride, (b) a carboxylated amphoteric polymer compound obtained by reacting ε-poly-L-lysine with butyl succinic anhydride and succinic anhydride, or (c) a carboxylated amphoteric polymer compound obtained by reacting ε-poly-L-lysine with a compound represented by formula I; and (d) a sucrose polymer macromolecule to which epichlorohydrin has been crosslinked.

12 Claims, 26 Drawing Sheets

(56) References Cited

OTHER PUBLICATIONS

International Preliminary Report on Patentability (Forrn PCT/IB/338) issued in counterpart International Application No. PCT/JP2016/071169 dated Dec. 14, 2017, with Form PCT/IB/373 and PCT/ISA/237 (9 pages).

Office Action dated Aug. 18, 2021 in Japanese Patent Application No. 2018-500176, with English-language translation.

* cited by examiner

[FIG. 1]
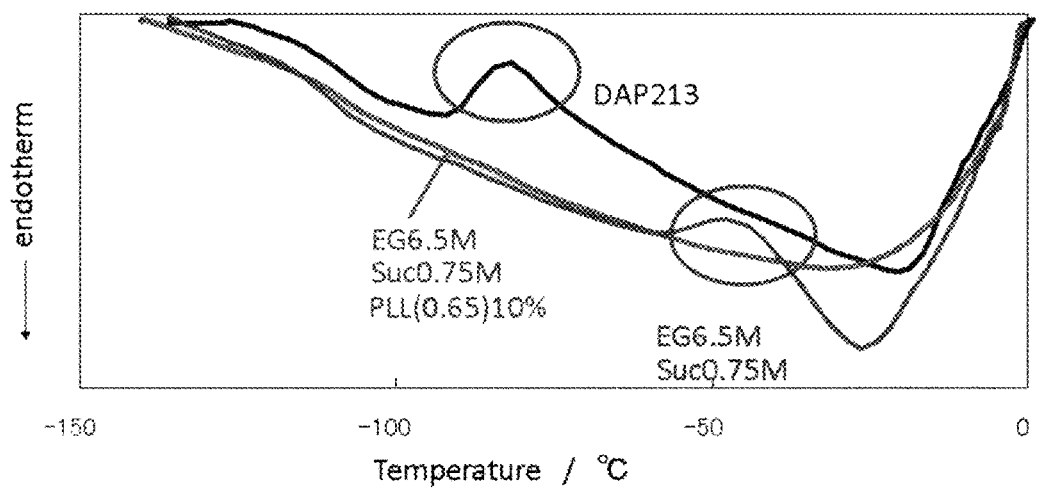
[FIG 2a]
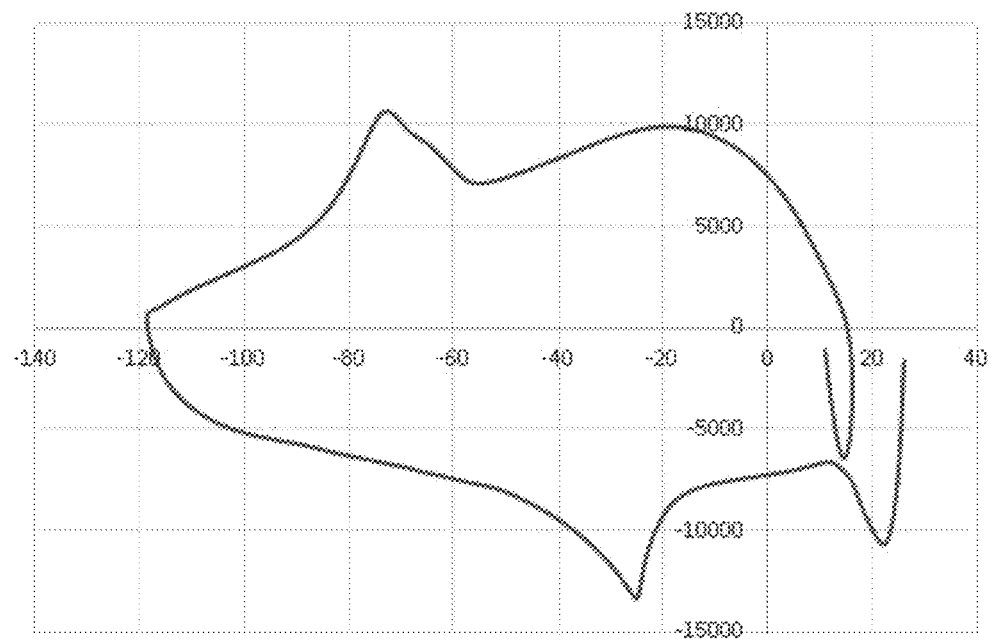

[FIG. 2b]
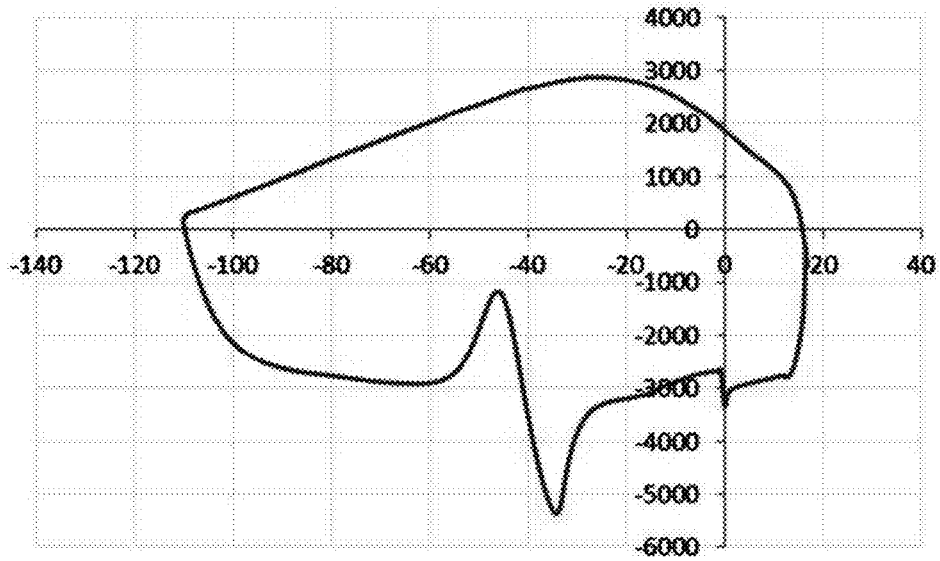
[FIG. 2c]
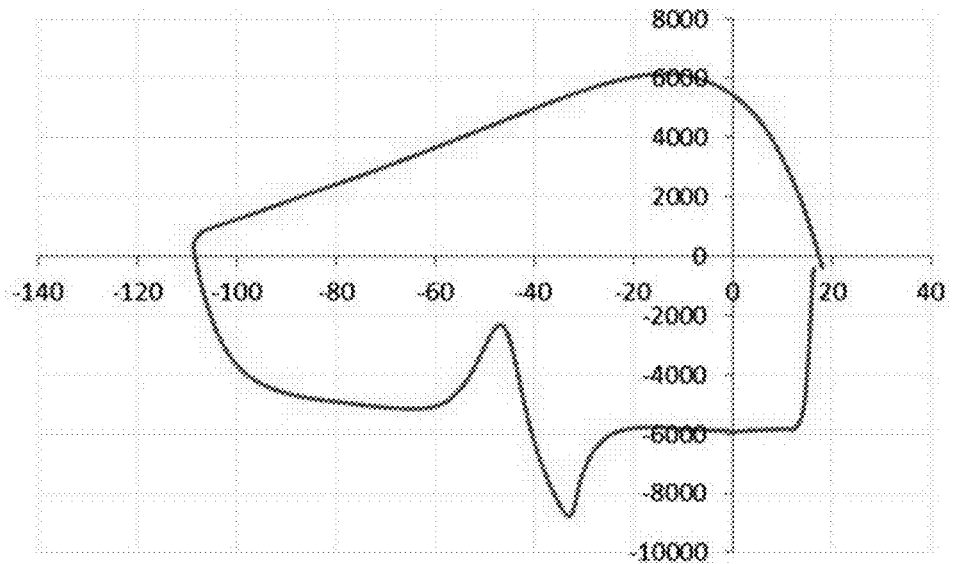

[FIG. 3a]
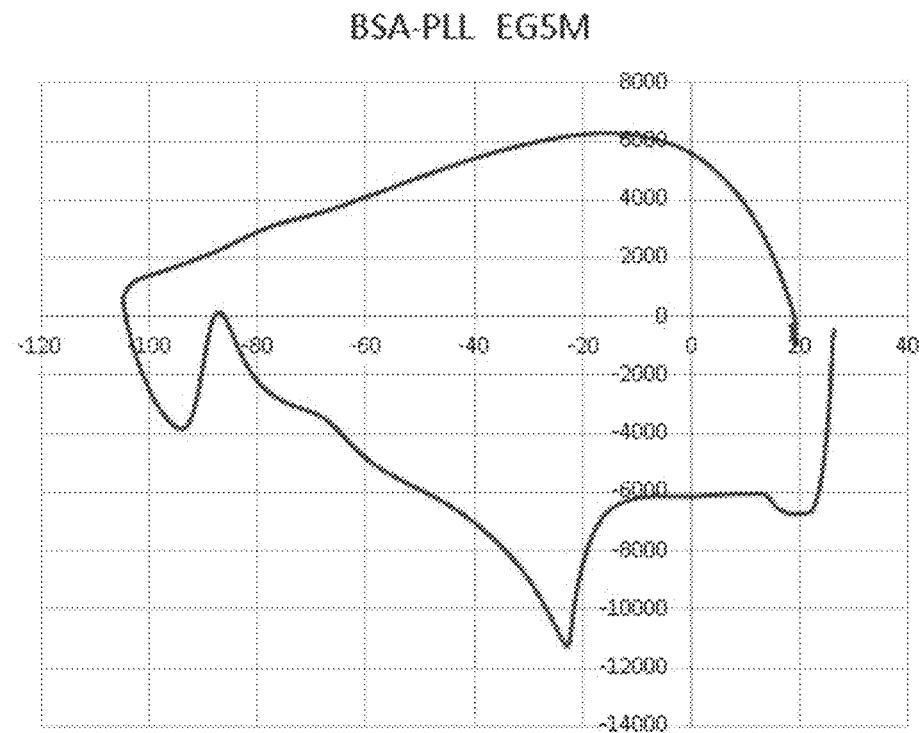
[FIG. 3b]
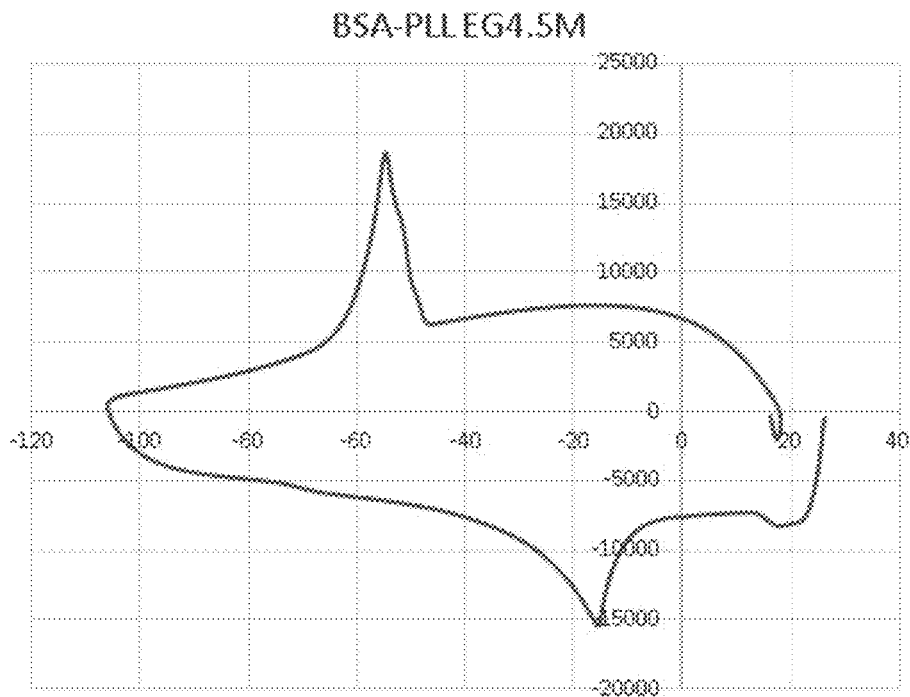

[FIG. 4]
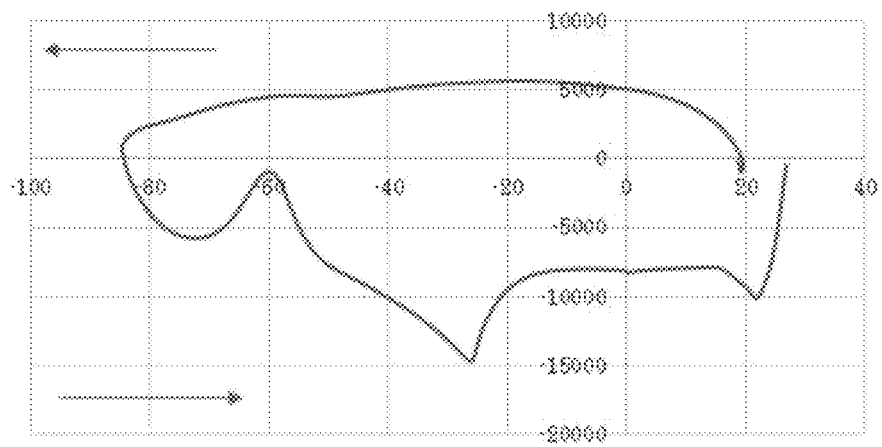
[FIG. 5a]
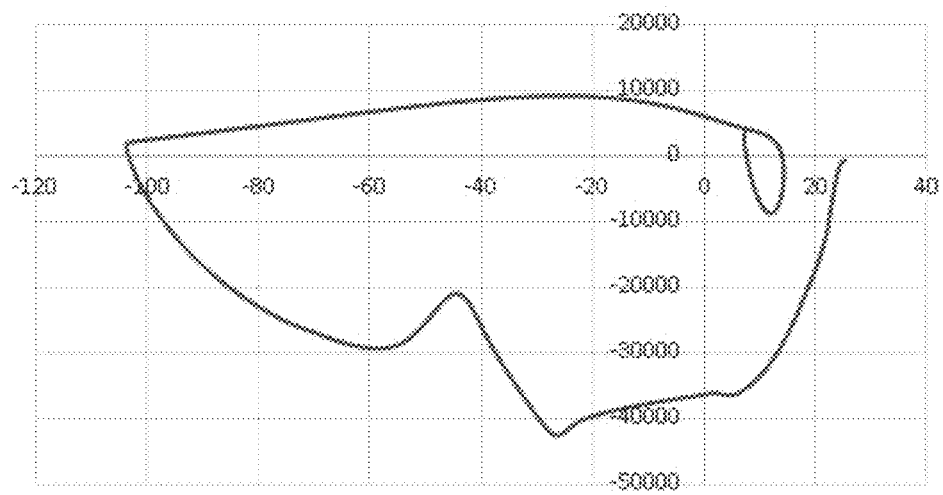

[FIG. 5b]
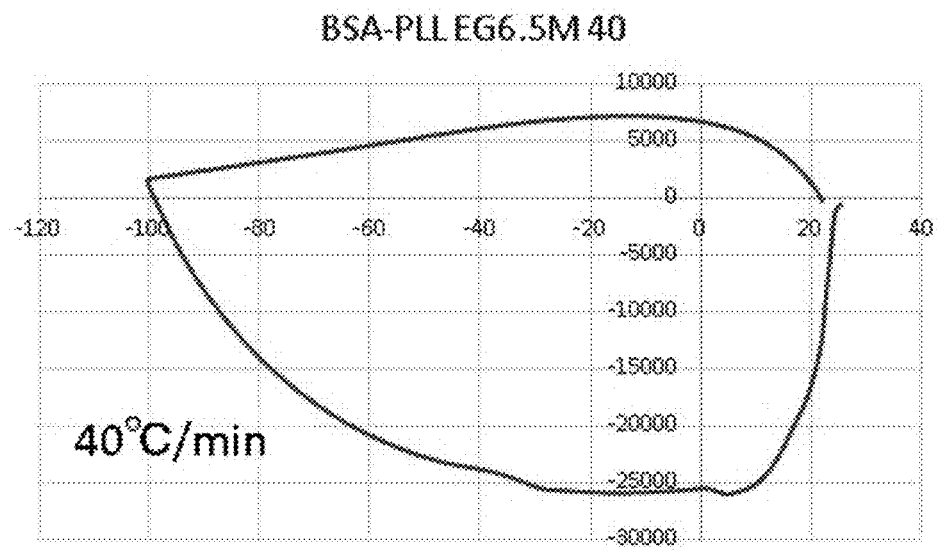
[FIG. 5c]
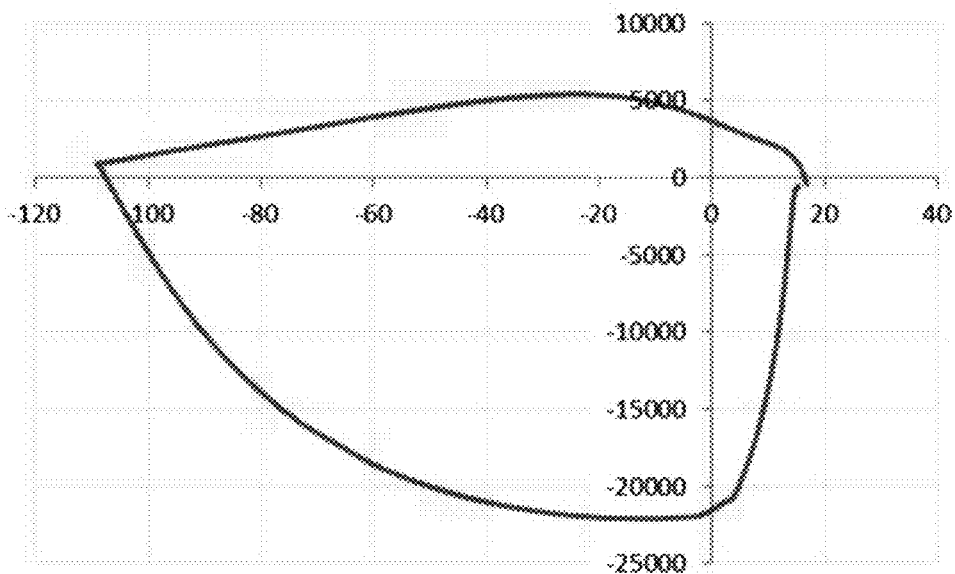

[FIG. 6a]
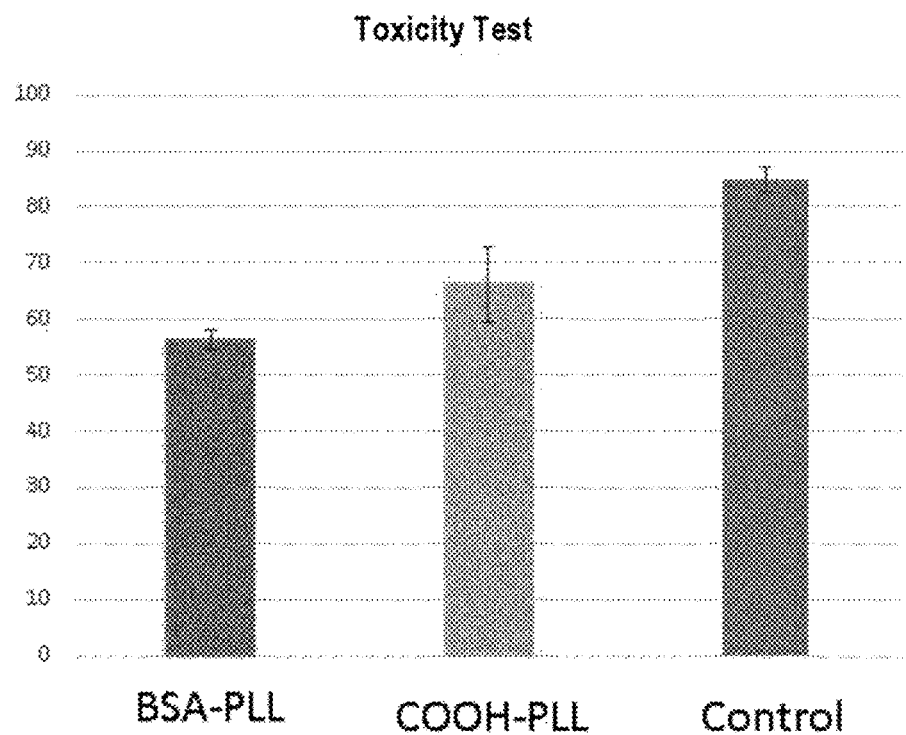
[FIG. 6b]
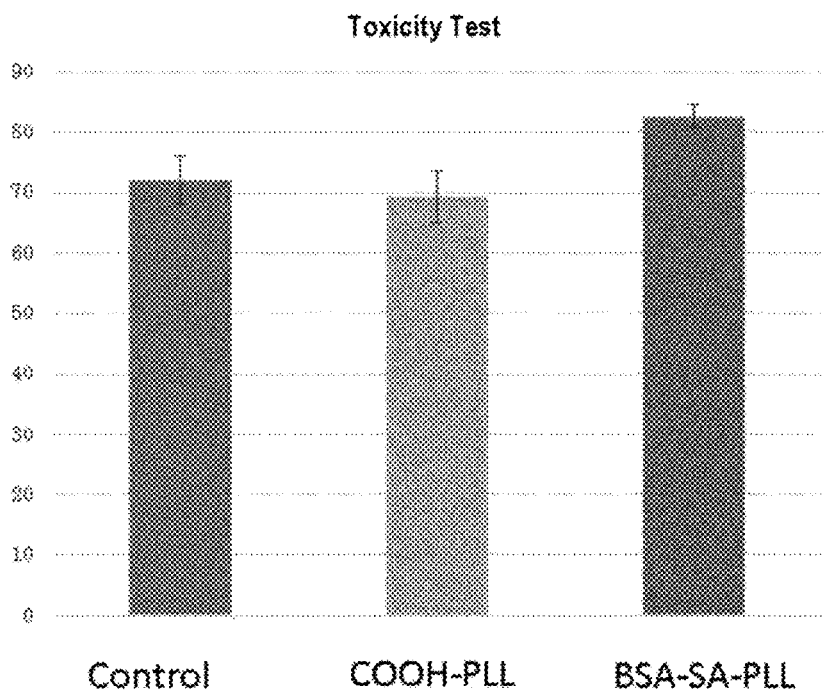

[FIG. 7a]
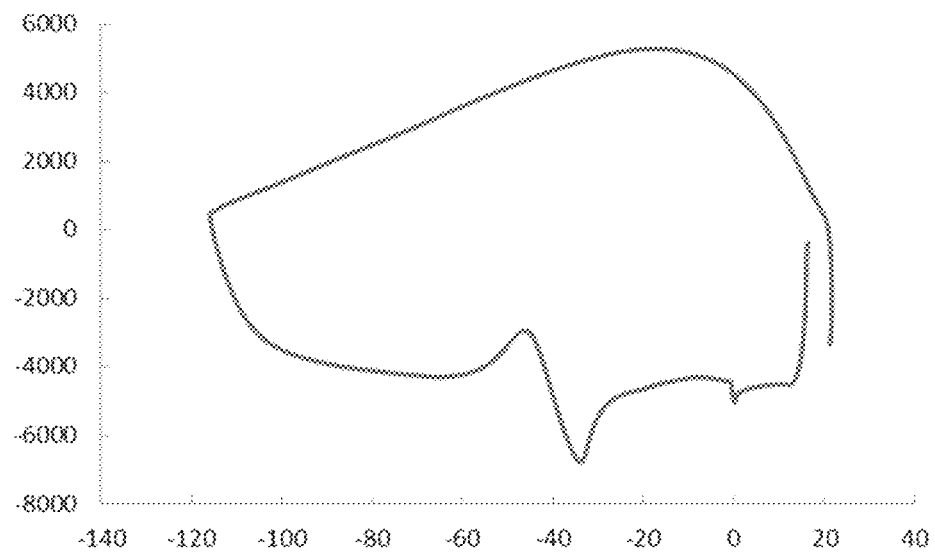
[FIG. 7b]
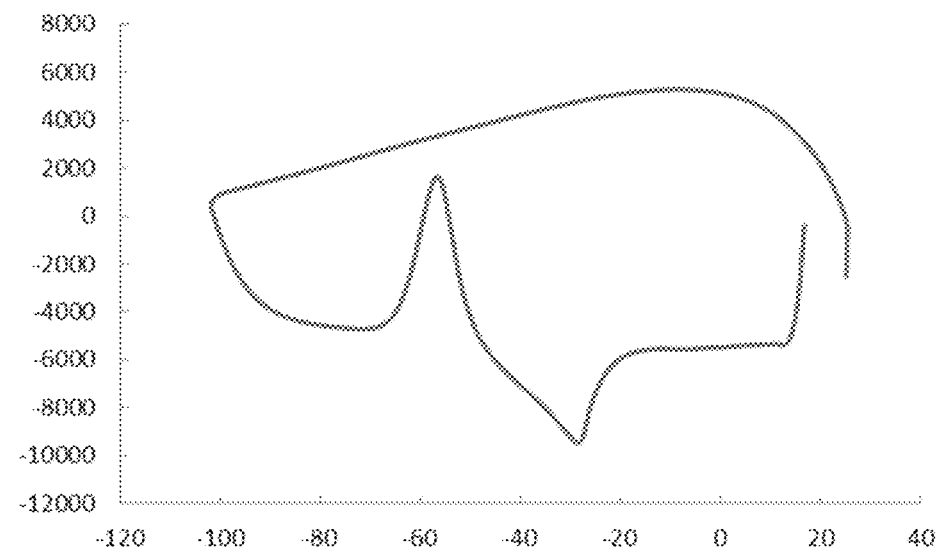

[FIG. 7c]
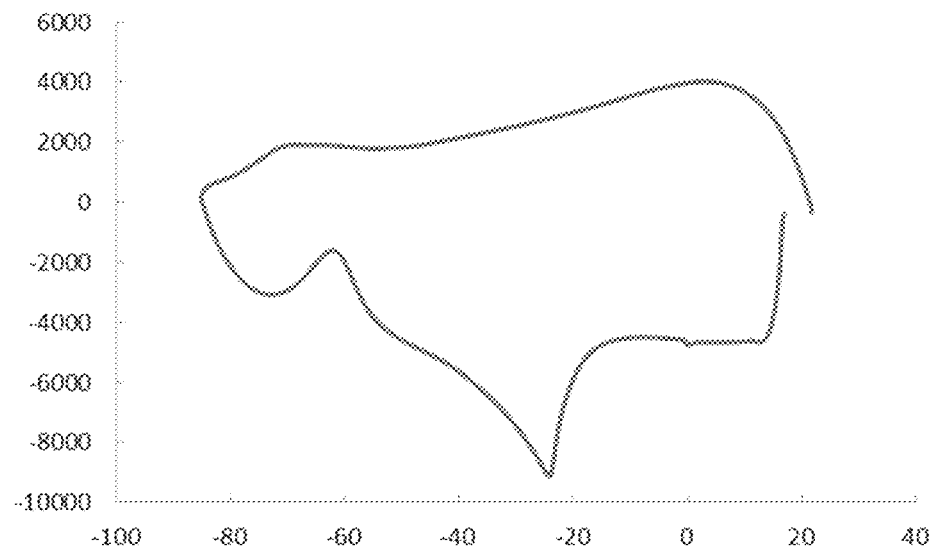
[FIG. 7d]
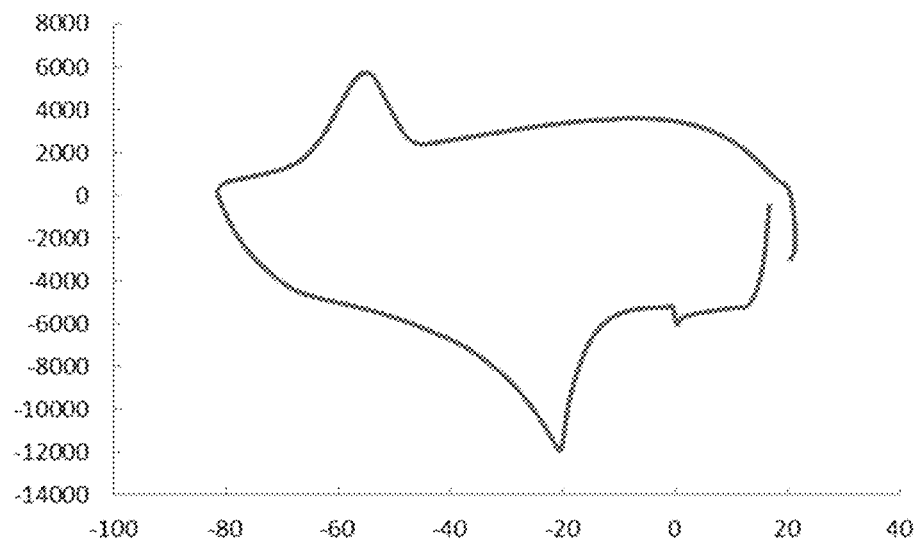

[FIG. 8]
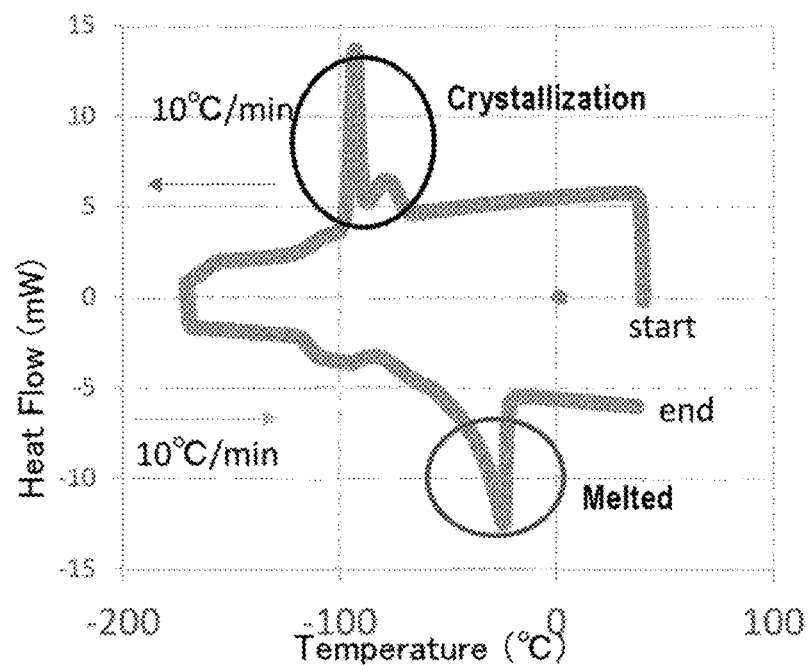
[FIG. 9]
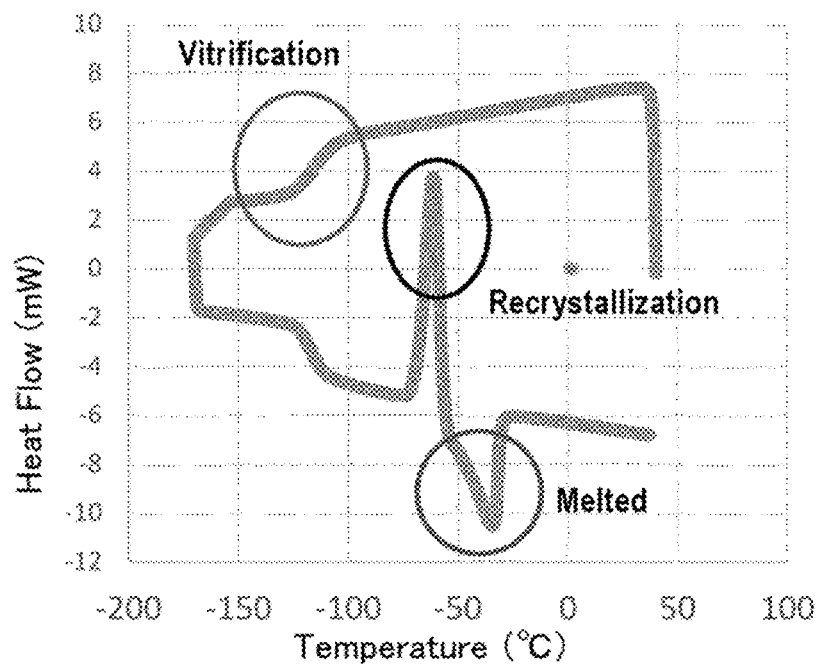

[FIG. 10a]
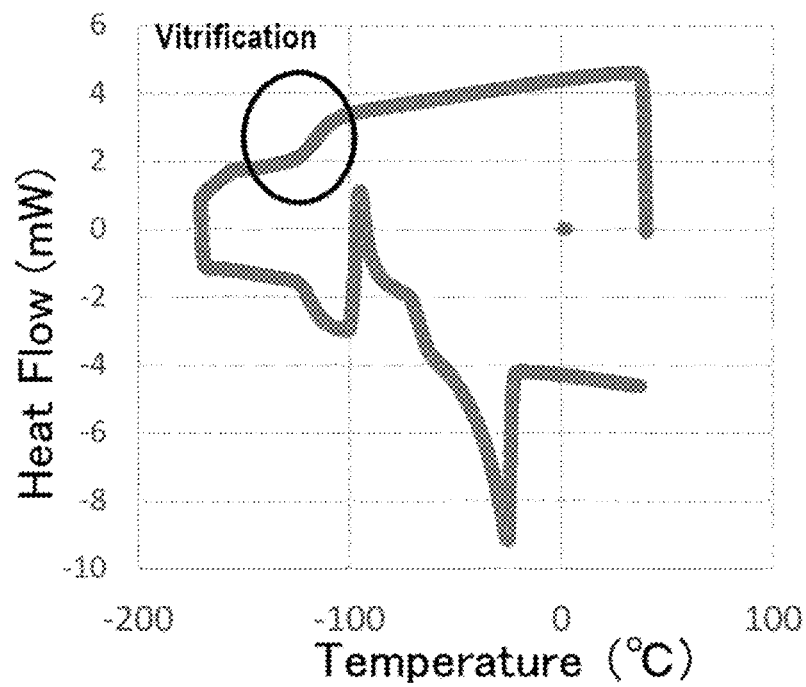
[FIG. 10b]
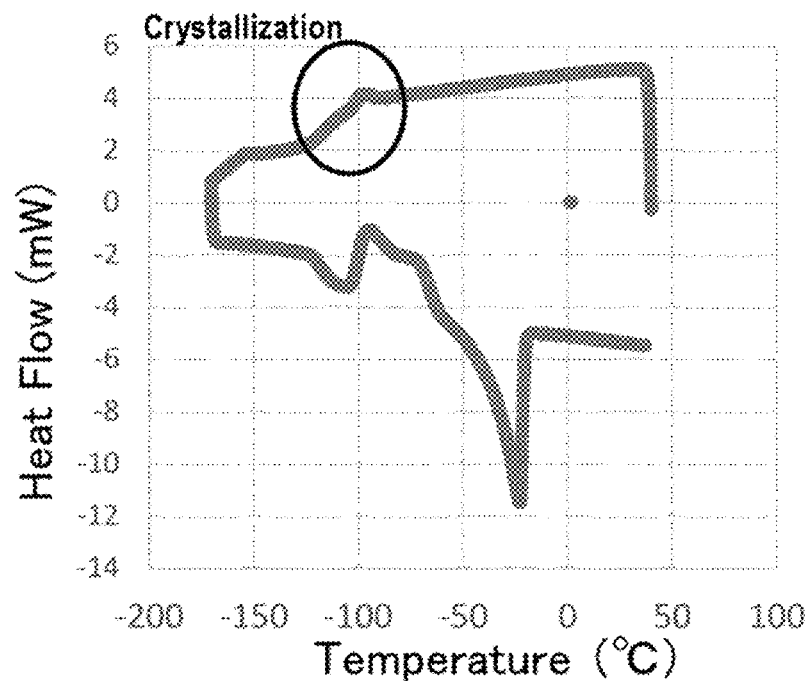

[FIG. 11a]
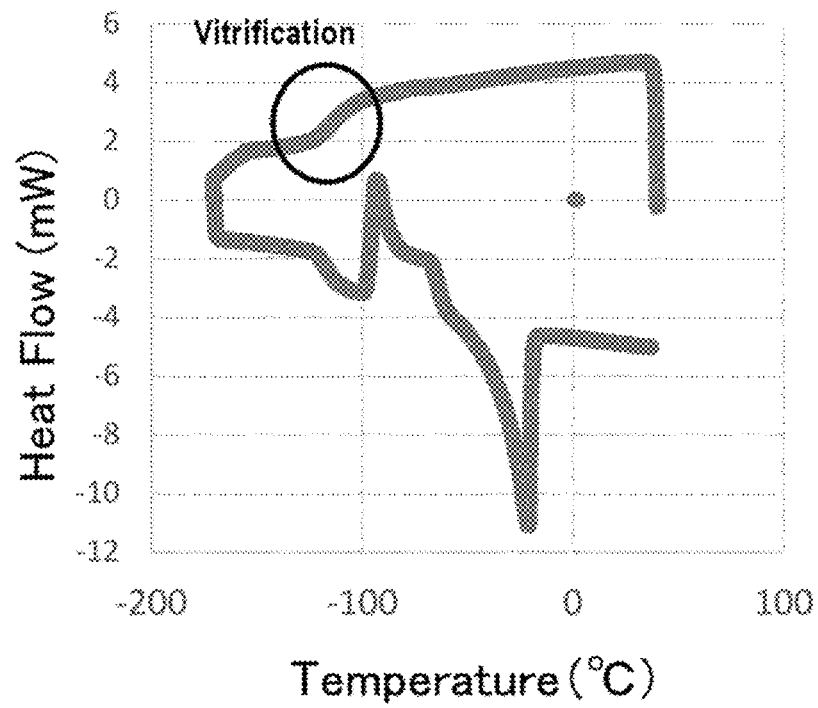
[FIG. 11b]
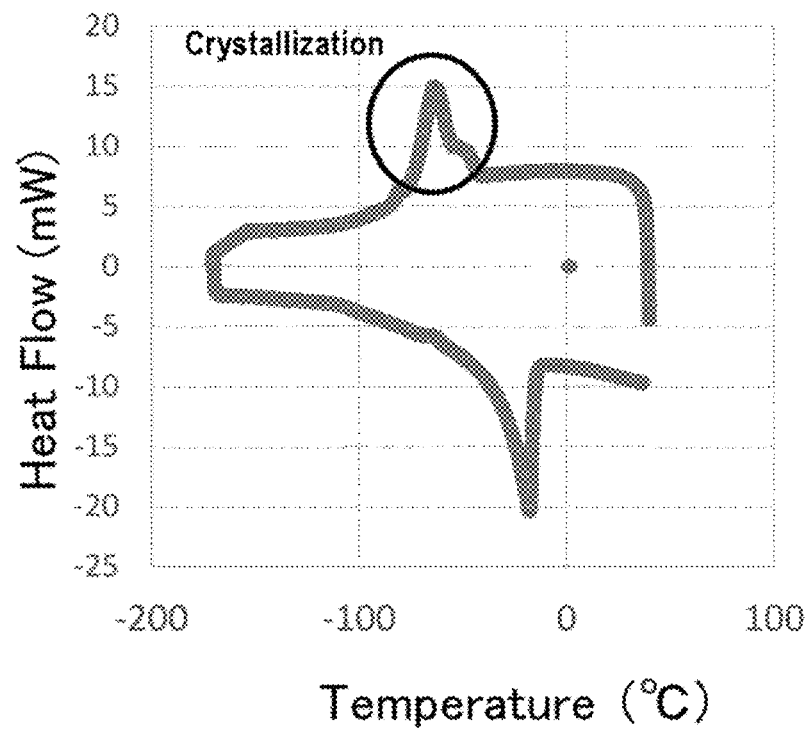

[FIG. 12a]
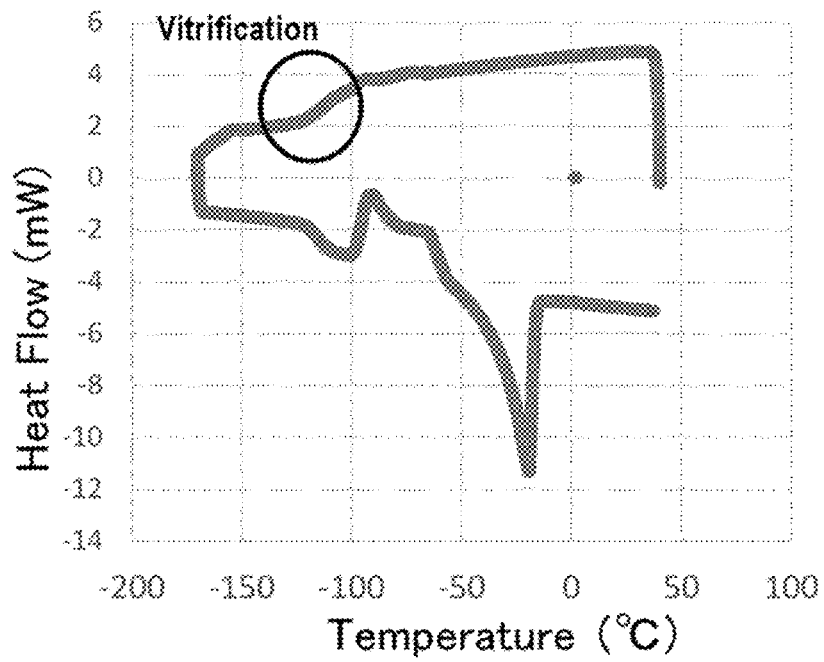
[FIG. 12b]
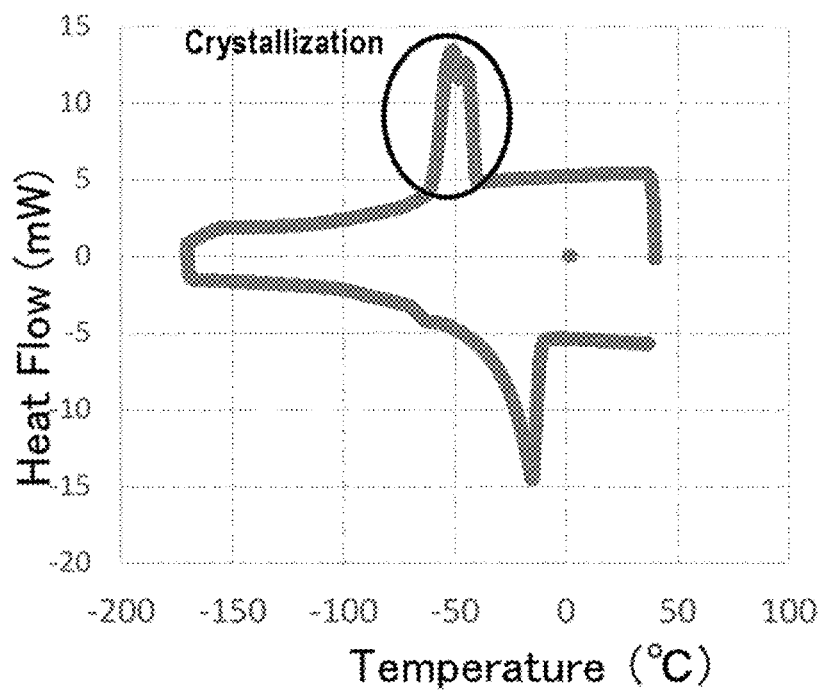

[FIG. 13a]
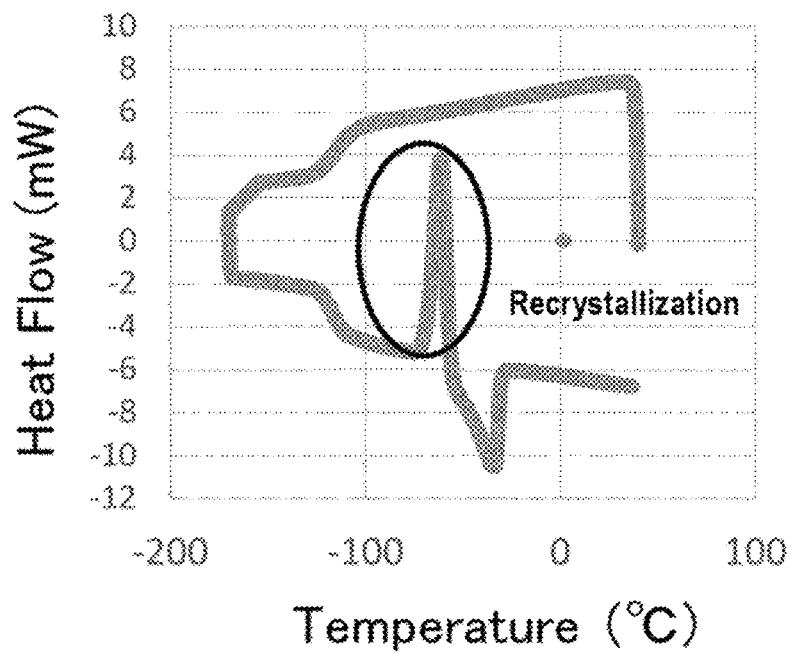
[FIG. 13b]
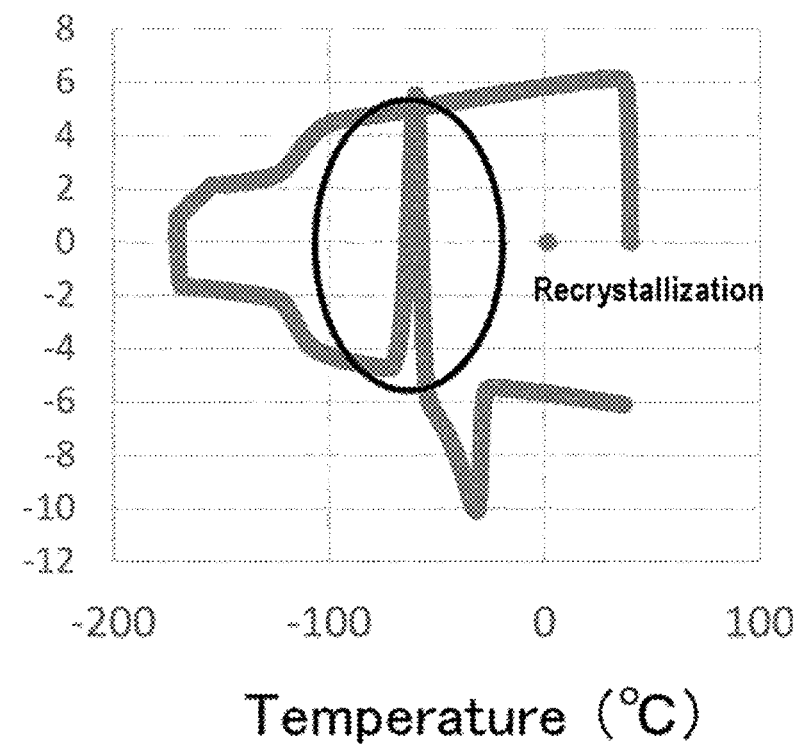

[FIG. 13c]
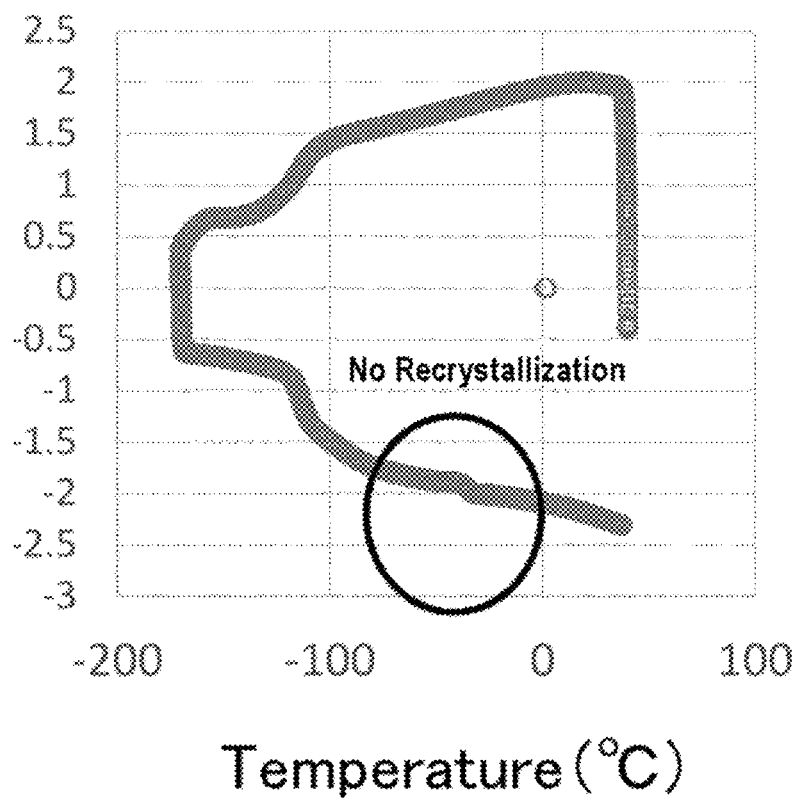
[FIG. 14a]
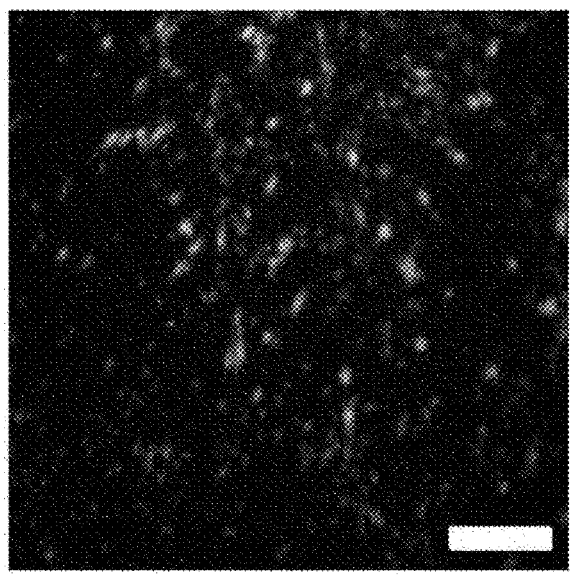

[FIG. 14b]
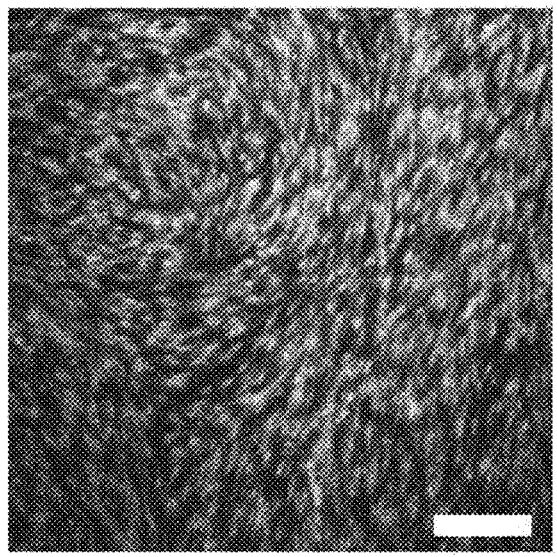
[FIG. 14c]
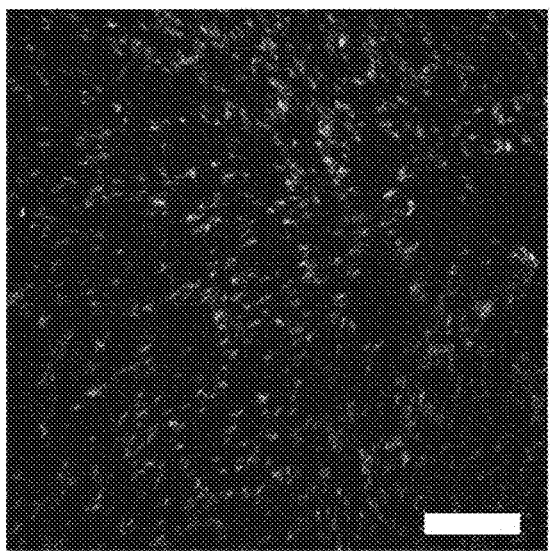

[FIG. 14d]
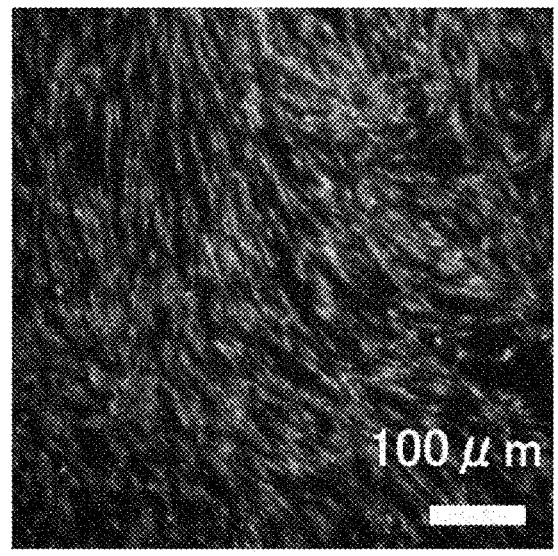
[FIG. 15]
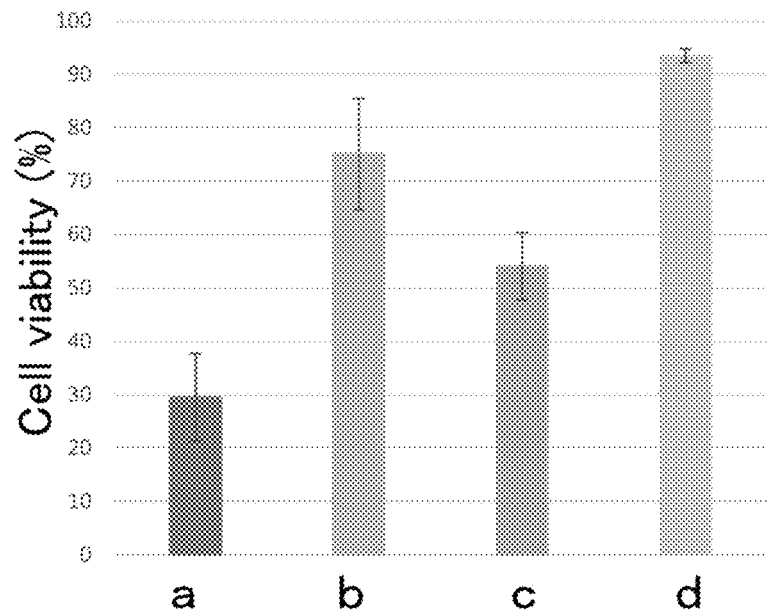

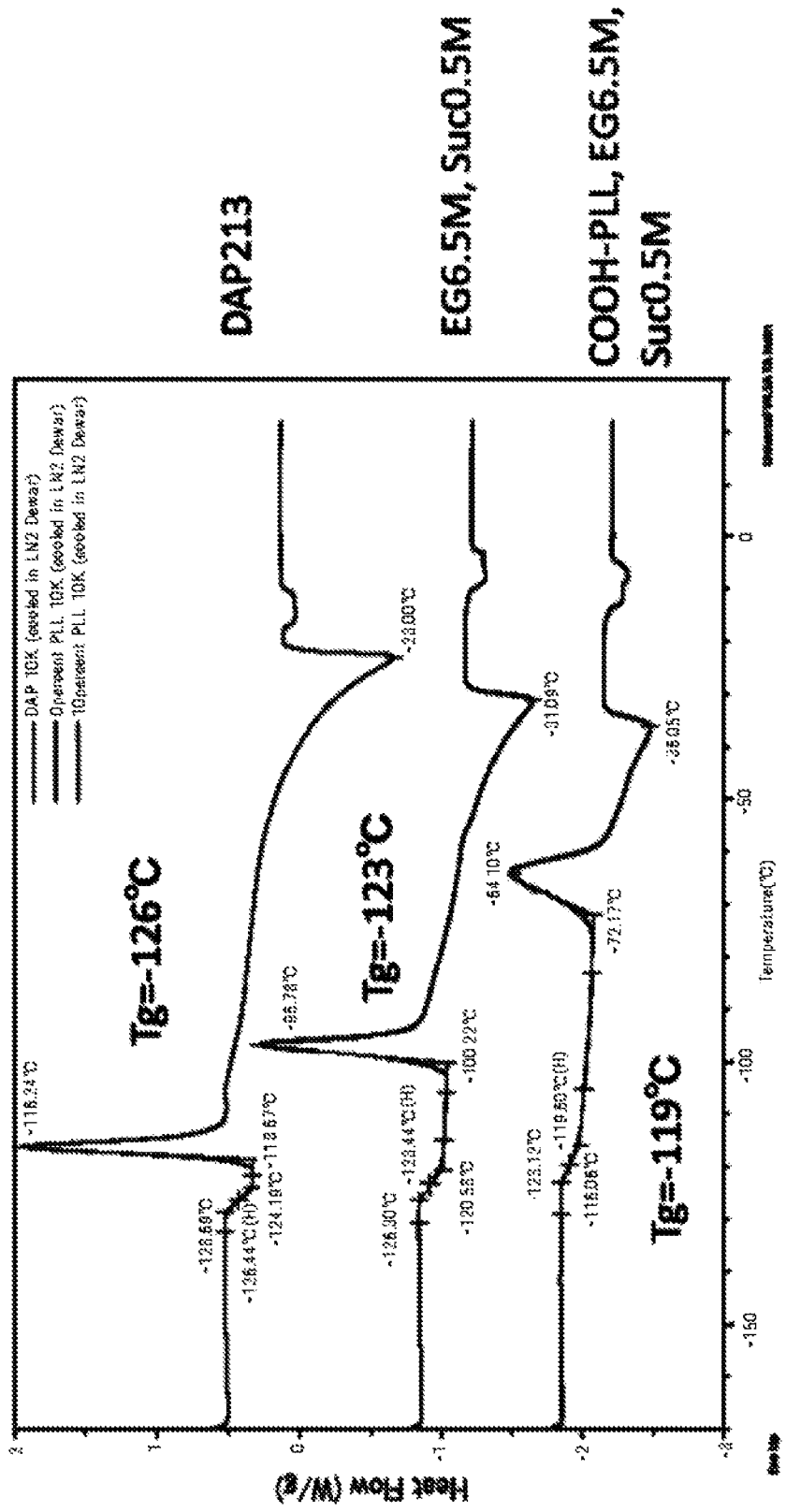
[FIG. 16]

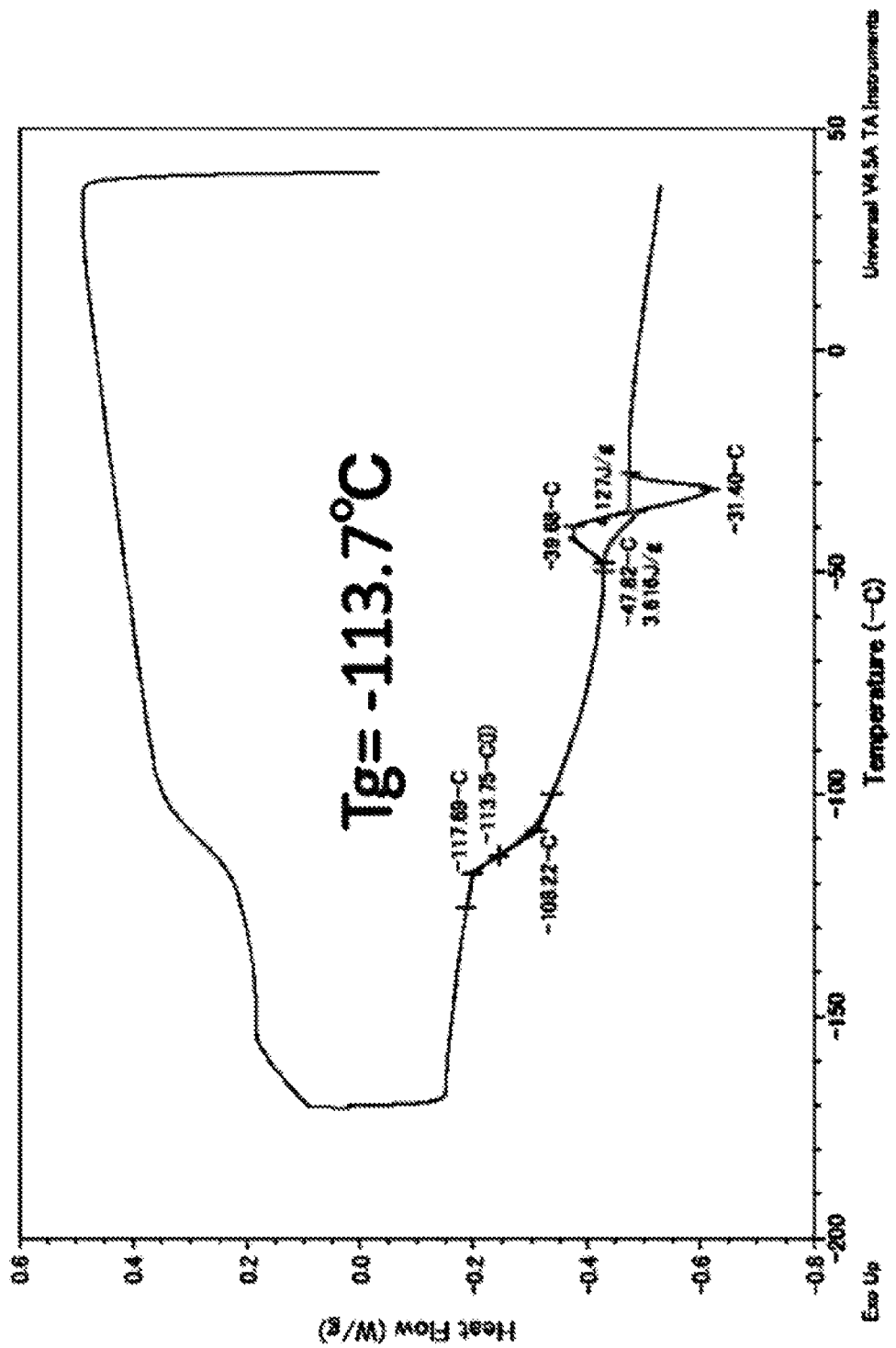
[FIG. 17]

[FIG. 18]
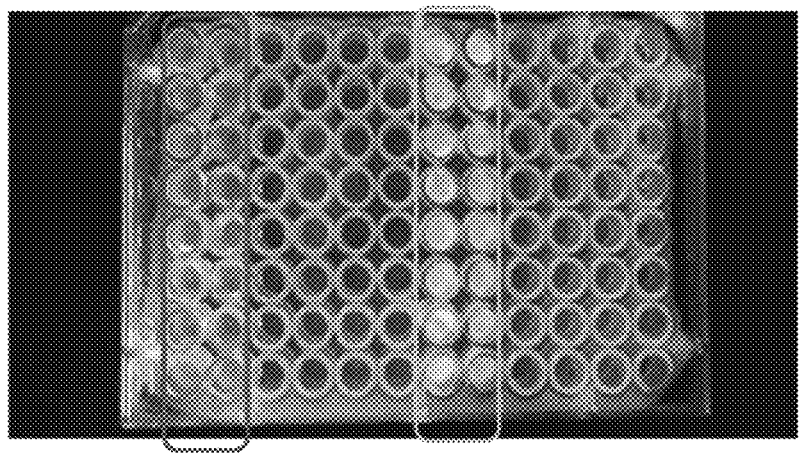
[FIG. 19]
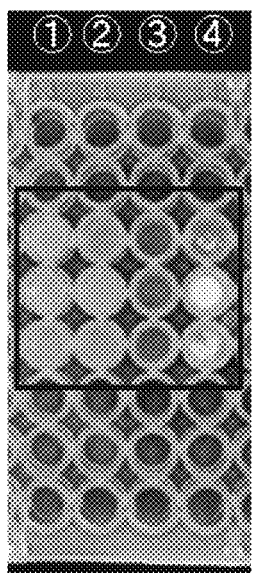

[FIG. 20a]
EG6M, Suc0.5M
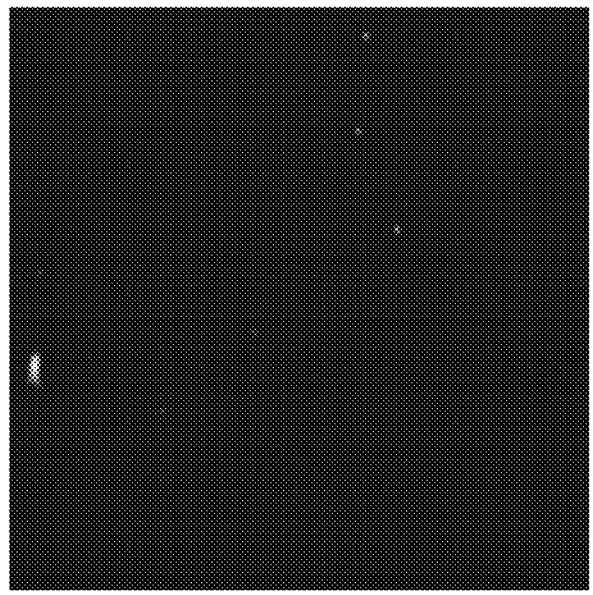
[FIG. 20b]
COOH-PLL 25mM,
EG6M, Suc0.5M
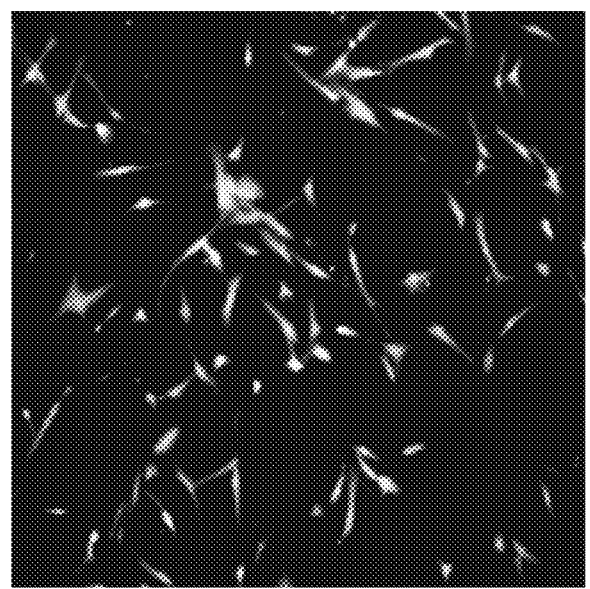

[FIG. 20c]
DMGA-PLL 25mM,
EG6M, Suc0.5M
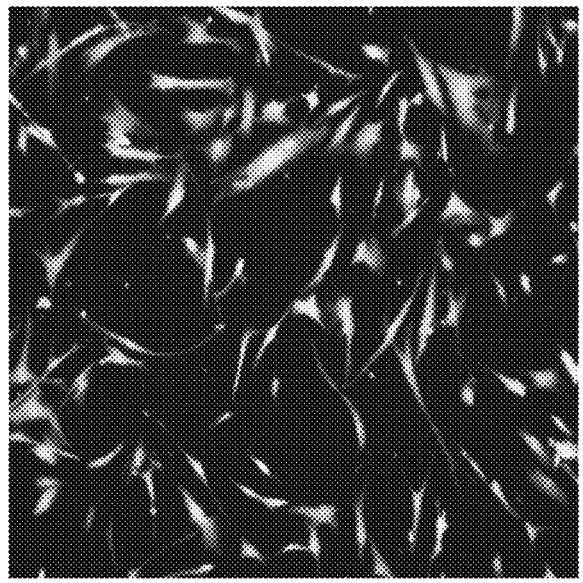
[FIG. 20d]
DMGA-PLL 25mM,
EG6M, Suc0.5M,
Ficoll 10%

[FIG. 21a]
EG6M, Suc0.5M
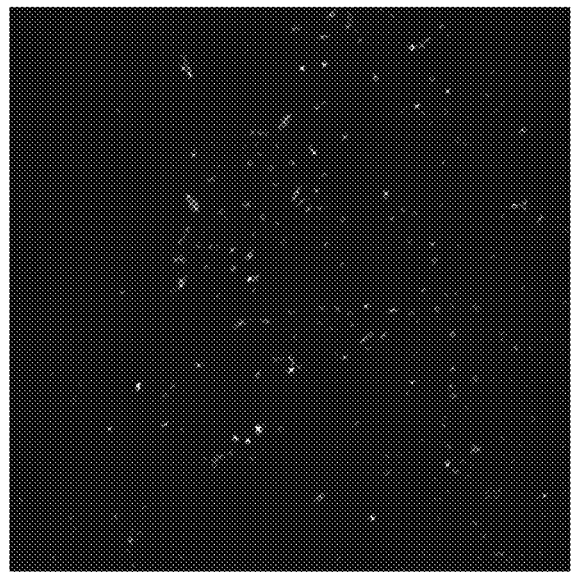
[FIG. 21b]
COOH-PLL 25mM,
EG6M, Suc0.5M
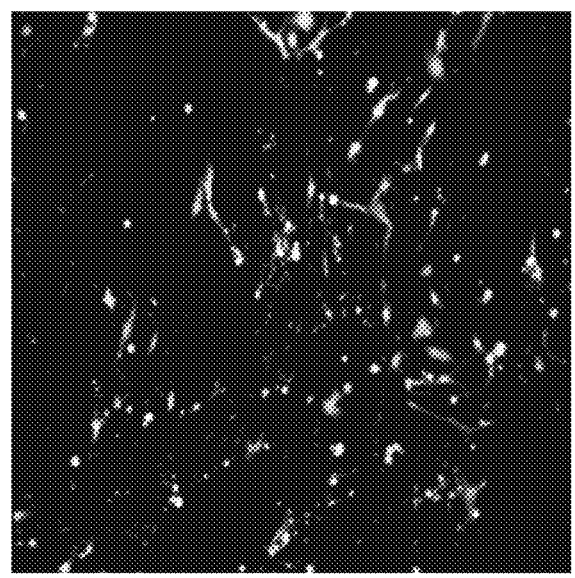

[FIG. 21c]
DMGA-PLL 25mM, EG6M, Suc0.5M
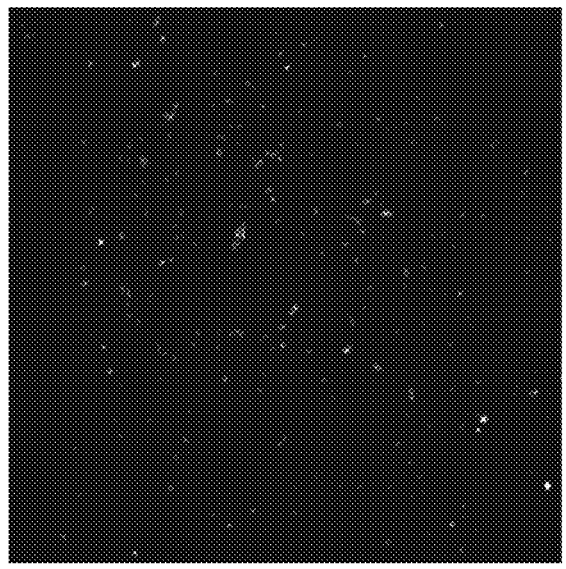
[FIG. 21d]
DMGA-PLL 25mM, EG6M, Suc0.5M, Ficoll 10%
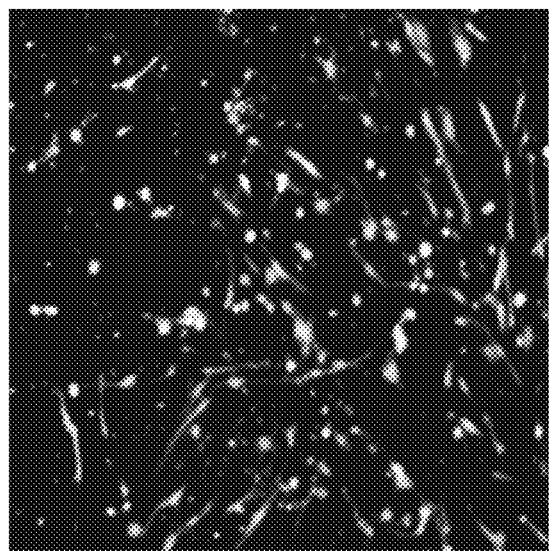

VITREOUS STATE STABILIZING AGENT FOR ANIMAL CELL CRYOPRESERVATION SOLUTION

TECHNICAL FIELD

The present invention relates to a vitreous state stabilizing agent for an animal cell cryopreservation solution, and an animal cell cryopreservation solution containing the vitreous state stabilizing agent.

BACKGROUND ART

Recently, expectations for clinical applications of regenerative medicines have increased. To this end, a basic technique has been required for cryopreservation of cells, cell sheets, three-dimensional cell structures and tissues. Such a technique includes cryopreserving the targets while adding a cryoprotective agent to prevent damage to the targets. As such a cryoprotective agent, dimethyl sulfoxide (DMSO) (O=S(CH)$_2$), glycerin and the like are known.

DMSO and glycerin have been sufficiently proven for use in cryopreservation for dispersed cells. However, when used in cryopreservation for the cell sheets, three-dimensional cell structures, tissues and the like, DMSO and glycerin often cause a damaged state after thawing, leaving damage. Based on consideration that the damage might be caused by ice crystal formation or dewatering shrinkage during freezing, a vitrifying method has been attempted, which controls ice crystallization and allows solidification in an amorphous state.

The vitrifying method has been developed as a method of freezing fertilized eggs, and the conventional vitrifying method is generally intended to vitrify an aqueous solution by a rapid freezing rate and high concentration of a solute. For example, DAP 213 is known as the vitrifying solution for fertilized eggs of mice. DAP 213 is a solution containing 2 M of DMSO, 1 M of acetamide and 3 M of propylene glycol, which has high concentration and high toxicity. A typical use is to replace water contained in the fertilized eggs of mice with the solution and directly immerse them in liquid nitrogen to provide a vitreous state. However, vitrification with such a vitrifying solution would result in higher cytotoxicity and further higher damage due to recrystallization during thawing.

Therefore, the present inventors have made an attempt to improve the vitrifying method by investigating the cryoprotective agent (Patent Document 1).

Patent Document 2 discloses production of a sucrose polymer macromolecule.

CITATION LIST

Patent Literatures

Patent Document 1: Japanese Patent No. 5630979 B
Patent Document 2: U.S. Pat. No. 3,300,474

SUMMARY OF INVENTION

Technical Problem

The cryopreservation solution containing carboxylated polylysine disclosed in Patent Document 1 exhibits good vitrification ability, but there is a need for a novel cryopreservation solution having improved vitrification ability.

Accordingly, an object of the present invention is to provide a novel animal cell cryopreservation solution having improved vitrification ability.

Solution to Problem

As a result of intensive studies, the present inventors have found that the above object can be achieved by an animal cell cryopreservation solution using an polyampholyte shown below as a vitreous state stabilizing agent for an animal cell cryopreservation solution, and have completed the present invention.

Thus, the present invention includes the following aspects (1) to (17):

(1)
A vitreous state stabilizing agent for an animal cell cryopreservation solution, comprising: at least one polyampholyte having amino groups and carboxyl groups in the same molecule; and (d) at least one epichlorohydrin-crosslinked sucrose polymer macromolecule, the polyampholyte being selected from the group consisting of the following (a), (b) and (c):
(a) at least one carboxylated polyampholyte resulting from reaction of ε-poly-L-lysine with butylsuccinic anhydride;
(b) at least one carboxylated polyampholyte resulting from reaction of ε-poly-L-lysine with butylsuccinic anhydride and succinic anhydride; or
(c) at least one carboxylated polyampholyte resulting from reaction of ε-poly-L-lysine with a compound represented by the following formula (I):

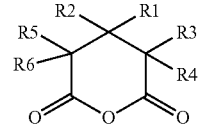

Formula (I)

in which:
R1 and R2 each independently represents a hydrogen atom or a C1 to C4 alkyl group, or R1 and R2 together form a C1 to C6 alkane-diyl group;
R3 and R4 each independently represents a hydrogen atom or a C1 to C4 alkyl group, or R3 and R4 together form a C1 to C6 alkane-diyl group;
R5 and R6 each independently represents a hydrogen atom or a C1 to C4 alkyl group, or R5 and R6 together form a C1 to C6 alkane-diyl group.

(2)
The vitreous state stabilizing agent for the animal cell cryopreservation solution according to the aspect (1), wherein the compound represented by the formula (I) comprises a compound represented by the following formula (II):

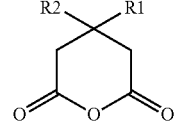

Formula (II)

in which:
R1 and R2 each independently represents a hydrogen atom or a C1 to C4 alkyl group, or R1 and R2 together form a C1 to C6 alkane-diyl group.

(3)

The vitreous state stabilizing agent for the animal cell cryopreservation solution according to the aspect (1) or (2), wherein the at least one polyampholyte has a percentage of carboxylated amino groups among the amino groups in the side chains of ε-poly-L-lysine, in a range of from 50% to 75%.

(4)

The vitreous state stabilizing agent for the animal cell cryopreservation solution according to any one of the aspects (1) to (3), wherein the at least one carboxylated polyampholyte resulting from reaction of ε-poly-L-lysine with butylsuccinic anhydride and succinic anhydride has a ratio B/A of a number B of carboxylated amino groups resulting from reaction with butylsuccinic anhydride among the amino groups in the side chains of ε-poly-L-lysine to a number A of carboxylated amino acids resulting from reaction with succinic anhydride among the amino groups in the side chains of ε-poly-L-lysine, in a range of from 2/30 to 40/30.

(5)

The vitreous state stabilizing agent for the animal cell cryopreservation solution according to any one of the aspects (1) to (4), wherein the epichlorohydrin-crosslinked sucrose polymer macromolecule has a molecular weight in a range of from 10,000 to 1,000,000.

(6)

An animal cell cryopreservation solution comprising a physiological solution, the physiological solution containing the vitreous state stabilizing agent for the animal cell cryopreservation solution according to any one of the aspects (1) to (5).

(7)

An animal cell cryopreservation solution comprising a physiological solution, the physiological solution containing:
the vitreous state stabilizing agent for the animal cell cryopreservation solution according to any one of the aspects (1) to (5); and
ethylene glycol or propylene glycol at a concentration of from 3 to 8 M.

(8)

The animal cell cryopreservation solution according to the aspect (7), further comprising sucrose at a concentration of from 0.1 to 1 M.

(9)

The animal cell cryopreservation solution according to any one of the aspects (6) to (8), wherein the animal cell cryopreservation solution comprises:
2 to 40% by weight of the polyampholyte selected from the group consisting of (a), (b) and (c); and
1 to 30% by weight of the epichlorohydrin-crosslinked sucrose polymer macromolecule.

(10)

The animal cell cryopreservation solution according to any one of the aspects (6) to (9), wherein the animal cell cryopreservation solution has a glass transition point of from −135° C. to −80° C.

(11)

A method for cryopreserving animal cells, comprising the steps of:
immersing the animal cells in the animal cell cryopreservation solution according to any one of the aspects (6) to (10); and
freezing the animal cells in the animal cell cryopreservation solution by lowering a temperature.

(12)

The method for cryopreserving the animal cells according to the aspect (11), further comprising, after the step of freezing the animal cells in the animal cell cryopreservation solution by lowering the temperature, a step of thawing the frozen animal cells in the animal cell cryopreservation solution by elevating a temperature.

(13)

The method for cryopreserving the animal cells according to the aspect (11) or (12), wherein the step of freezing the animal cells in the animal cell cryopreservation solution by lowering the temperature comprises freezing the animal cells in a vitreous state by lowering the temperature.

(14)

The method for cryopreserving the animal cells according to the aspect (12) or (13), wherein the step of thawing the frozen animal cells in the animal cell cryopreservation solution by elevating the temperature comprises thawing the animal cells by elevating the temperature without recrystallization.

(15)

The method for cryopreserving the animal cells according to any one of the aspects (11) to (14), wherein the step of freezing the animal cells in the animal cell cryopreservation solution by lowering the temperature comprises freezing the animal cells by lowering the temperature at a cooling rate of from 5° C./min to 50° C./min.

(16)

The method for cryopreserving the animal cells according to any one of the aspects (12) to (15), wherein the step of thawing the frozen animal cells in the animal cell cryopreservation solution by elevating the temperature comprises thawing the frozen animal cells by elevating the temperature at a heating rate of from 5° C./min to 100° C./min.

(17)

The method for cryopreserving the animal cells according to any one of the aspects (12) to (16), wherein the method comprises, after the step of freezing the animal cells in the animal cell cryopreservation solution by lowering the temperature and before the step of thawing the frozen animal cells in the animal cell cryopreservation solution by elevating the temperature, a step of preserving the frozen animal cells in the animal cell cryopreservation solution at a temperature of from −196° C. to −75° C.

Advantageous Effects of Invention

According to the present invention, an animal cell cryopreservation solution having improved vitrification ability can be obtained. The use of the animal cell cryopreservation solution can result in suppression of crystallization even at a slower heating rate than that of prior art, allowing cryopreservation while maintaining the vitreous state. Further, it can result in suppression of recrystallization even during the temperature elevating, allowing thawing while stably maintaining the vitreous state. Therefore, according to the animal cell cryopreservation solution of the present invention, animal cells can be frozen and thawed with higher viability.

BRIEF DESCRIPTION OF DRAWINGS

FIG. 1 is a graph showing results of DSC measurement of conventional vitrifying solutions at a heating rate of 50° C./min.

FIG. 2a is a graph showing a result of crystallization evaluation by DSC measurement of a vitrifying solution containing COOH-PLL.

FIG. 2b is a graph showing a result of crystallization evaluation by DSC measurement of a vitrifying solution containing BSA-PLL.

FIG. 2c is a graph showing a result of crystallization evaluation by DSC measurement of a vitrifying solution containing BSA(35)-SA(30)-PLL.

FIG. 3a is a graph showing a result of crystallization evaluation by DSC measurement of a vitrifying solution containing BSA-PLL, EG 5M.

FIG. 3b is a graph showing a result of crystallization evaluation by DSC measurement of a vitrifying solution containing BSA-PLL, EG 4.5M.

FIG. 4 is a graph showing a result of crystallization evaluation by DSC measurement of a vitrifying solution containing BSA(35)-SA(30)-PLL, EG 5.5 M.

FIG. 5a is a graph showing a result of recrystallization evaluation by DSC measurement of a vitrifying solution containing COOH-PLL.

FIG. 5b is a graph showing a result of recrystallization evaluation by DSC measurement of a vitrifying solution containing BSA-PLL.

FIG. 5c is a graph showing a result of recrystallization evaluation by DSC measurement of a vitrifying solution containing BSA(35)-SA(30)-PLL.

FIG. 6a is a graph showing cell viability according to the respective vitrifying solutions.

FIG. 6b is a graph showing cell viability according to the respective vitrifying solutions.

FIG. 7a is a graph showing a result of crystallization evaluation by DSC measurement of a vitrifying solution containing DMGA-PLL, EG 6M.

FIG. 7b is a graph showing a result of crystallization evaluation by DSC measurement of a vitrifying solution containing DMGA-PLL, EG 5M.

FIG. 7c is a graph showing a result of crystallization evaluation by DSC measurement of a vitrifying solution containing DMGA-PLL, EG 4.5M.

FIG. 7d is a graph showing a result of crystallization evaluation by DSC measurement of a vitrifying solution containing DMGA-PLL, EG 4M.

FIG. 8 is a graph showing a result of crystallization evaluation by DSC measurement of a vitrifying solution containing EG 6.5M.

FIG. 9 is a graph showing a result of crystallization evaluation by DSC measurement of a vitrifying solution containing COOH-PLL, EG 6.5M.

FIG. 10a is a graph showing a result of crystallization evaluation by DSC measurement of a vitrifying solution containing COOH-PLL, EG 5.5M.

FIG. 10b is a graph showing a result of crystallization evaluation by DSC measurement of a vitrifying solution containing COOH-PLL, EG 5M.

FIG. 11a is a graph showing a result of crystallization evaluation by DSC measurement of a vitrifying solution containing BSA-PLL, EG 5M.

FIG. 11b is a graph showing a result of crystallization evaluation by DSC measurement of a vitrifying solution containing BSA-PLL, EG 4.5M.

FIG. 12a is a graph showing a result of crystallization evaluation by DSC measurement of a vitrifying solution containing DMGA-PLL, EG 4.5M.

FIG. 12b is a graph showing a result of crystallization evaluation by DSC measurement of a vitrifying solution containing DMGA-PLL, EG 4M.

FIG. 13a is a graph showing a result of crystallization evaluation by DSC measurement of a vitrifying solution containing COOH-PLL, EG 6M.

FIG. 13b is a graph showing a result of crystallization evaluation by DSC measurement of a vitrifying solution containing BSA-PLL, EG 6M.

FIG. 13c is a graph showing a results of crystallization evaluation by DSC measurement of a vitrifying solution containing DMGA-PLL, EG 6M.

FIG. 14a is a fluorescence microscopy photograph of a double-stained cell sheet frozen and thawed with a vitrifying solution containing EG 6M.

FIG. 14b is a fluorescence microscopy photograph of a double-stained cell sheet frozen and thawed with a vitrifying solution containing COOH-PLL, EG 6M.

FIG. 14c is a fluorescence microscopy photograph of a double-stained cell sheet frozen and thawed with a vitrifying solution containing BSA-PLL, EG 6M.

FIG. 14d is a fluorescence microscopy photograph of a double-stained cell sheet frozen and thawed with a vitrifying solution containing DMGA-PLL, EG 6M.

FIG. 15 is a graph showing cell viability after freezing and thawing cells in the respective vitrifying solutions.

FIG. 16 is a graph showing recrystallization behavior of various vitrifying solutions.

FIG. 17 is a graph showing recrystallization behavior of a DMGA-PLL vitrifying solution (DMGA-PLL 25 mM, Su 0.5 M and EG 6.0 M, Ficoll 10%).

FIG. 18 shows a photograph showing appearance after leaving a vitrifying solution obtained by adding 25 mM of DMGA-PLL or COOH-PLL (SA-PLL) to a solution of EG 6 M, sucrose 0.5 M and ficoll 10% to stand at −80° C. for 3 hours.

FIG. 19 is a photograph showing appearance after leaving vitrifying solutions obtained by respectively adding polysaccharides to solutions of EG 6 M, sucrose 0.5 M and DMGA 25 mM to stand at −80° C. for 3 hours.

FIG. 20a is a fluorescence microscopy photograph of a MSC sheet obtained by leaving the MSC sheet with a vitrifying solution (EG 6 M, Su 0.5 M) to stand in a freezer at −80° C. for 1 hour and then double-staining the MSC sheet.

FIG. 20b is a fluorescence microscopy photograph of a MSC sheet obtained by leaving the MSC sheet with a vitrifying solution (COOH-PLL 25 mM, EG 6 M, Su 0.5 M) to stand in a freezer at −80° C. for 1 hour, and then double-staining the MSC sheet.

FIG. 20c is a fluorescence microscopy photograph of a MSC sheet obtained by leaving the MSC sheet with a vitrifying solution (DMGA-PLL 25 mM, EG 6 M, Su 0.5 M) to stand in a freezer at −80° C. for 1 hour, and then double-staining the MSC sheet.

FIG. 20d is a fluorescence microscopy photograph of MSC sheet obtained by leaving the MSC sheet with a vitrifying solution (DMGA-PLL 25 mM, EG 6 M, Su 0.5 M, Ficoll 10%) to stand in a freezer at −80° C. for 1 hour, and then double-staining the MSC sheet.

FIG. 21a is a fluorescence microscopy photograph of a MSC sheet obtained by leaving the MSC sheet with a vitrifying solution (EG 6 M, Su 0.5 M) to stand in a freezer at −80° C. for 1 day, and then double-staining the MSC sheet.

FIG. 21b is a fluorescence microscopy photograph of a MSC sheet obtained by leaving the MSC sheet with a vitrifying solution (COOH-PLL 25 mM, EG 6 M, Su 0.5 M) to stand in a freezer at −80° C. for 1 day, and then double-staining the MSC sheet.

FIG. 21c is a fluorescence microscopy photograph of a MSC sheet obtained by leaving the MSC sheet with a vitrifying solution (DMGA-PLL 25 mM, EG 6 M, Su 0.5 M) to stand in a freezer at −80° C. for 1 day, and then double-staining the MSC sheet.

FIG. 21d is a fluorescence microscopy photograph of a MSC sheet obtained by leaving the MSC sheet with a vitrifying solution (DMGA-PLL 25 mM, EG 6 M, Su 0.5 M, Ficoll 10%) to stand in a freezer at −80° C. for 1 day, and then double-staining the MSC sheet.

DESCRIPTION OF THE PREFERRED EMBODIMENTS

Figure 22:
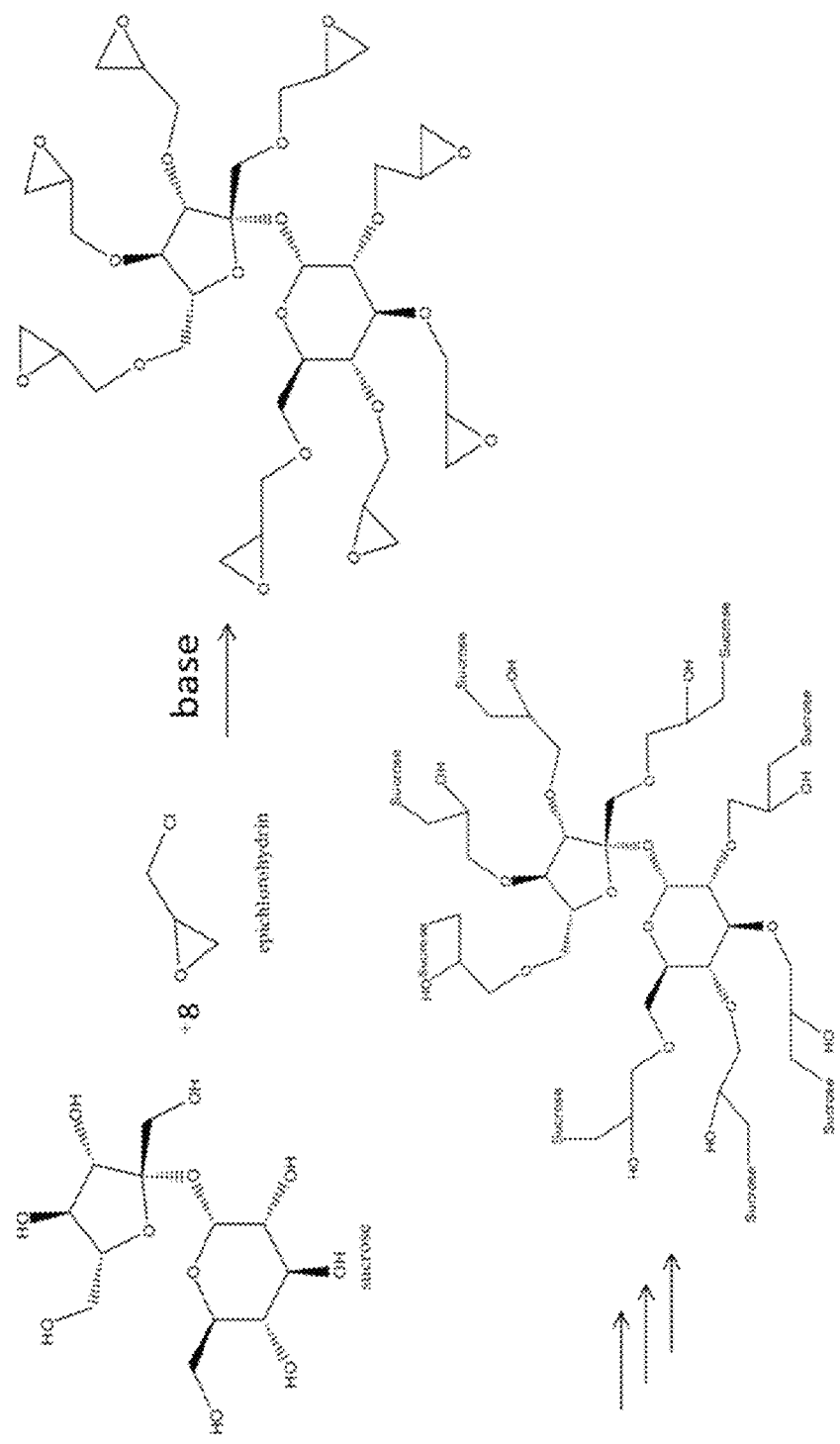
FIG. 22 illustrates the scheme of the crosslinking sucrose with epichlorohydrin.

The present invention will be described in detail below with reference to specific embodiments. The present invention is not limited to the following specific embodiments.

[Vitreous State Stabilizing Agent for Animal Cell Cryopreservation Solution]

The present invention relates to a vitreous state stabilizing agent for an animal cell cryopreservation solution, comprising: at least one polyampholyte having amino groups and carboxyl groups in the same molecule, selected from the group consisting of the following (a), (b) and (c); and (d) at least one epichlorohydrin-crosslinked sucrose polymer macromolecule:
(a) at least one carboxylated polyampholyte resulting from reaction of ε-poly-L-lysine with butylsuccinic anhydride;
(b) at least one carboxylated polyampholyte resulting from reaction of ε-poly-L-lysine with butylsuccinic anhydride and succinic anhydride; or
(c) at least one carboxylated polyampholyte resulting from reaction of ε-poly-L-lysine with a compound represented by the formula (I):

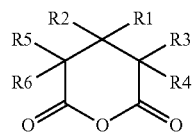

Formula (I)

in which:
R1 and R2 each independently represents a hydrogen atom or a C1 to C4 alkyl group, or R1 and R2 together form a C1 to C6 alkane-diyl group;
R3 and R4 each independently represents a hydrogen atom or a C1 to C4 alkyl group, or R3 and R4 together form a C1 to C6 alkane-diyl group;
R5 and R6 each independently represents a hydrogen atom or a C1 to C4 alkyl group, or R5 and R6 together form a C1 to C6 alkane-diyl group.

[ε-poly-L-lysine]

For the ε-poly-L-lysine, known ε-poly-L-lysine may be used. The ε-poly-L-lysine may have a molecular weight of from 100 to 100,000 for example, and in a preferred embodiment, the ε-poly-L-lysine that can be used includes those having a number average molecular weight of, for example from 1,000 to 20,000 or from 1,000 to 10,000, produced by microorganisms or enzymes. The ε-poly-L-lysine is produced by actinomycete belonging to the genus *Streptomyces* and is exclusively used as a food ingredient. Further, attempts have been made to produce ε-poly-L-lysine having a degree of polymerization of 20 or less, in addition to a degree of polymerization of 15 to 35. The number average molecular weight or the number average degree of polymerization can be easily measured by SDS-PAGE (sodium dodecyl sulfate-polyacrylamide gel electrophoresis), for example using an electrophoresis apparatus and a densitograph (model AE-6920V) available from ATTO Corporation. It is also possible to use those having a molecular weight of 30,000 or more obtained by increasing the molecular weight with a heat treatment. The polylysine having a free carboxyl group only at its terminal contains primary amino groups in its side chains, and the amino groups are carboxylated by the reaction that will be described below.

[Carboxylation of Amino Group of ε-Poly-L-Lysine]

The polyampholyte having amino groups and carboxyl groups in the same molecule can have a percentage of carboxylated amino groups among the amino groups in the side chains of ε-poly-L-lysine, for example in a range of from 50% to 75%, or in a range of from 60% to 70%.

[BSA-PLL]

As shown in the chemical reaction scheme described in Examples, butylsuccinic anhydride (BSA) reacts with the amino groups in the side chains of ε-poly-L-lysine (PLL) to form a carboxylated polyampholyte (BSA-PLL) which is the polyampholyte having amino groups and carboxyl groups in the same molecule and is the vitreous state stabilizing agent for the animal cell cryopreservation solution according to the present invention.

[BSA-SA-PLL]

The amino groups in the side chains of ε-poly-L-lysine (PLL) reacts with butylsuccinic anhydride (BSA) and succinic anhydride (SA) to form a carboxylated polyampholyte (BSA-SA-PLL) which is the polyampholyte having amino groups and carboxyl groups in the same molecule and is the vitreous state stabilizing agent for the animal cell cryopreservation solution according to the present invention. Butylsuccinic anhydride and succinic anhydride may simultaneously react with ε-poly-L-lysine, or one of butylsuccinic anhydride and succinic anhydride may firstly react with ε-poly-L-lysine and other may then react with ε-poly-L-lysine. A ratio B/A of a number B of carboxylated amino groups resulting from reaction with butylsuccinic anhydride among the amino groups in the side chains of ε-poly-L-lysine to a number A of carboxylated amino groups resulting from reaction with succinic anhydride among the amino groups in the side chains of ε-poly-L-lysine may be in a range of from 2/30 to 40/30, in a range of from 10/30 to 40/30, or in a range of form 30/40 to 40/30.

[GA-PLL]

A GA derivative (a glutaric anhydride derivative) represented by the following formula I reacts with the amino groups in the side chains of ε-poly-L-lysine to form a carboxylated polyampholyte (GA-PLL), which is the polyampholyte having amino groups and carboxyl groups in the same molecule and is the vitreous state stabilizing agent for the animal cell cryopreservation solution according to the present invention.

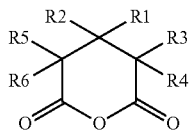

Formula (I)

In the formula as stated above, R1 and R2 can each independently represent a hydrogen atom or a C1 to C4 alkyl group, or R1 and R2 can together form a C1 to C6 alkane-diyl group. The C1 to C4 alkyl group may be, for example, a C1 to C3 or C1 to C2 alkyl group. Examples of the alkane-diyl group can include C1 to C3 alkane-1,1-diyl groups and C4 to C6 alkylene groups. Examples of the combination of R1 and R2 can include a hydrogen atom and a hydrogen atom; a hydrogen atom and a methyl group; a hydrogen atom and an ethyl group; a methyl group and a methyl group; a methyl group and an ethyl group; and an ethyl group and an ethyl group. Examples of the C1 to C3 alkane-1,1-diyl groups can include a methane-1,1-diyl group and an ethane-1,1-diyl group. Examples of the C4 to C6 alkylene groups can include a tetramethylene group (a butane-1,4-diyl group) and a pentamethylene group (a pentane-1,5-diyl group).

In the formula as stated above, R3 and R4 can each independently represent a hydrogen atom or a C1 to C4 alkyl group, or R3 and R4 can together form a C1 to C6 alkane-diyl group. The C1 to C4 alkyl group may be, for example, a C1 to C3 or C1 to C2 alkyl group. Examples of the alkane-diyl group can include C1 to C3 alkane-1,1-diyl groups and C4 to C6 alkylene groups. Examples of the combination of R3 and R4 can include a hydrogen atom and a hydrogen atom; a hydrogen atom and a methyl group; a hydrogen atom and an ethyl group; a methyl group and a methyl group; a methyl group and an ethyl group; and an ethyl group and an ethyl group. Examples of the C1 to C3 alkane-1,1-diyl groups can include a methane-1,1-diyl group and an ethane-1,1-diyl group. Examples of the C4 to C6 alkylene groups can include a tetramethylene group (a butane-1,4-diyl group) and a pentamethylene group (a pentane-1,5-diyl group).

In the formula as stated above, R5 and R6 can each independently represent a hydrogen atom or a C1 to C4 alkyl group, or R5 and R6 can together form a C1 to C6 alkane-diyl group. The C1 to C4 alkyl group may be, for example, a C1 to C3 or C1 to C2 alkyl group. Examples of the alkane-diyl group can include C1 to C3 alkane-1,1-diyl groups and C4 to C6 alkylene groups. Examples of the combination of R5 and R6 can include a hydrogen atom and a hydrogen atom; a hydrogen atom and a methyl group; a hydrogen atom and an ethyl group; a methyl group and a methyl group; a methyl group and an ethyl group; and an ethyl group and an ethyl group. Examples of the C1 to C3 alkane-1,1-diyl groups can include a methane-1,1-diyl group and an ethane-1,1-diyl group. Examples of the C4 to C6 alkylene groups can include a tetramethylene group (a butane-1,4-diyl group) and a pentamethylene group (a pentane-1,5-diylgroup).

In a preferred embodiment, R1 and R2 may be the groups as defined above, and R3, R4, R5 and R6 may be hydrogen atoms, in the above formula. That is, the GA derivative may be represented by the following formula II.

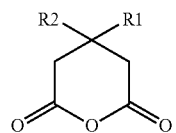

Formula (II)

In a preferred embodiment, R3 and R4 may be the groups as defined above, and R1, R2, R5 and R6 may be hydrogen atoms, in the above formula. That is, the GA derivative may be represented by the following formula. Needless to say, this GA derivative is equivalent to the GA derivative in which R5 and R6 are the groups as defined above, and R1, R2, R3 and R4 are hydrogen atoms, in the above formula.

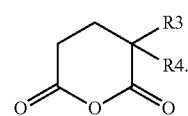

Formula (III)

Specific examples of such a GA derivative can include compounds having the following structures:

3,3-dimethylglutaric anhydride (DMGA):

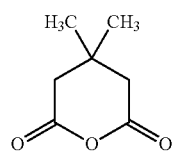

glutaric anhydride (GA):

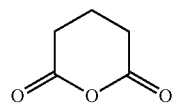

3-methylglutaric anhydride (MGA):

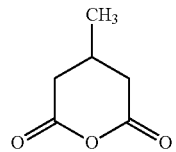

2,2-dimethylglutaric anhydride:

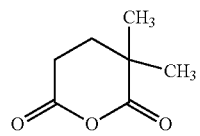

3,3-tetramethylene glutaric anhydride:

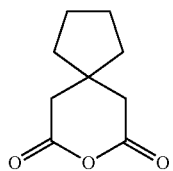

3-oxaspiro[5,5]undecane-2,4-dione (3,3-pentamethylene glutaric anhydride):

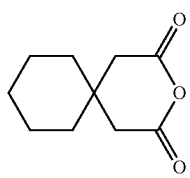 [SMILES: O=C1CC2(CCCCC2)CC(=O)O1]

[DMGA-PLL]

In a preferred embodiment, 3,3-dimethylglutaric anhydride (DMGA) can react with the amino groups in the side chains of ε-poly-L-lysine to provide a carboxylated polyampholyte (DMGA-PLL).

[Epichlorohydrin-Crosslinked Sucrose Polymer Macromolecule]

The epichlorohydrin-crosslinked sucrose polymer macromolecule is a water-soluble polymer composed of a sucrose polymer prepared by crosslinking sucrose with epichlorohydrin. The crosslinking with epichlorohydrin is generated by adding epichlorohydrin to a hydroxyl group in a sucrose molecule under a basic condition and adding the resulting epoxy to an adjacent hydroxyl group in the sucrose molecule. The reaction scheme of the crosslinking with epichlorohydrin is illustrated in FIG. 22.

The reaction scheme of FIG. 22 illustrates a case where epichlorohydrin is added to all the hydroxyl groups of sucrose. The epichlorohydrin-crosslinked sucrose polymer macromolecule thus produced has a structure of the following formula (IV):

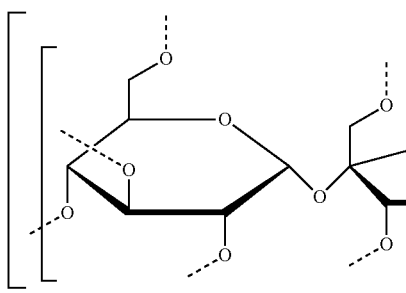 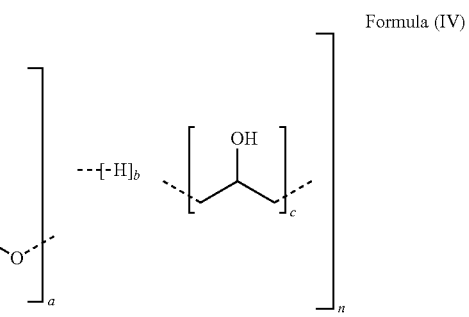

Formula (IV)

In the formulae (IV):
a represents 1;
b represents the number of hydroxyl groups remaining without reaction with epichlorohydrin (an average number per a sucrose unit), among hydroxyl groups of a sucrose unit, and is for example, in a range of from 0 to 8, from 1 to 6, or from 2 to 5 (with the exception of 8);

c represents the number of epichlorohydrin bridges: (O)—$CH_2$—CH(OH)—$CH_2$—(O) that links O (oxygen) to O (oxygen) which are derived from the hydroxyl groups of sucrose, and is, for example, in a range of from 0 to 8, from 1 to 6, or from 2 to 5 (with the exception of 0);
a, b and c satisfy the relational expression: 8×a=b+c;
n represents an average degree of polymerization of the sucrose polymer macromolecule, and is, for example, in a range of from 10 to 2,000, from 50 to 1,500, or from 100 to 1,200.

Specifically, synthesis of epichlorohydrin-crosslinked sucrose polymer macromolecule can be carried out according to the teachings of Examples 1, 4 and the like of Patent Document 2 (U.S. Pat. No. 3,300,474), for example. The resulting sucrose polymer macromolecule can be appropriately fractionated by a known means to obtain a fraction having a desired molecular weight. Examples of commercially available products can include Ficoll PM 70 (a molecular weight of 70,000) manufactured by GE Healthcare Ltd.

In a preferred embodiment, the molecular weight of the epichlorohydrin-crosslinked sucrose polymer macromolecule may be, for example, from 10,000 to 1,000,000, from 40,000 to 700,000, or from 50,000 to 500,000.

For example, the epichlorohydrin-crosslinked sucrose polymer macromolecule may be contained at a concentration of, for example, 0.1% by weight or more, 1% by weight or more, 2.5% by weight or more, 5% by weight or more, 7.5% by weight or more, 10% by weight or more, or 15% by weight or more, in the animal cell cryopreservation solution, or it may be contained at a concentration of, for example, 30% by weight or less, 25% by weight or less, or 20% by weight or less, and for example, it may be contained at a concentration of from 1% by weight to 30% by weight, from 7.5% by weight to 30% by weight, from 10% by weight to 30% by weight, or from 15% by weight to 25% by weight. A suitable concentration range can be adjusted by considering the types and concentrations of the polymer components in the animal cell cryopreservation solution, for example the concentrations of BSA-PLL, BSA-SA-PLL, GA-PLL, DMGA-PLL and the like, and by further considering the types and concentrations of other components, such as the concentrations of sucrose, ethylene glycol, propylene glycol, and the like.

[Animal Cell Cryopreservation Solution]

The animal cell cryopreservation solution according to the present invention is a physiological solution containing the vitreous state stabilizing agent for the animal cell cryopreservation solution as defined above. Examples of the physiological solution can include, but not particularly limited to, physiological saline solutions having a known composition, PBS, cell culture media, and the like. The vitreous state stabilizing agent for the animal cell cryopreservation solution may be contained in the animal cell cryopreservation solution, for example, in an amount of from 2 to 40% by weight, from 3 to 30% by weight, or from 5 to 20% by weight. Alternatively, when the polyampholyte has a molecular weight of from 2,000 to 20,000, the concentration of the vitreous state stabilizing agent may be from 1 to 100 mM, from 5 to 50 mM, or from 10 to 30 mM.

[Sucrose]

In a preferred embodiment, the animal cell cryopreservation solution may contain sucrose (Su). The content of sucrose may be, for example, in a range of from 0.1 to 1 M, or from 0.3 to 0.6 M.

[Ethylene Glycol and Propylene Glycol]

In a preferred embodiment, the animal cell cryopreservation solution may contain ethylene glycol (EG) or propylene glycol (PG), preferably ethylene glycol. Although ethylene glycol or the like is an effective component for the animal cell cryopreservation solution, it is preferable that the content is lesser in terms of cytotoxicity. According to the present invention, in order to be able to achieve a sufficiently improved vitrification ability while decreasing the content, the concentration of ethylene glycol to be used may be selected from, for example, ranges such as from 3 to 8 M, from 4 to 7 M, from 4.5 to 7 M, from 5 M to 7 M, 4 M or more and 4.5 M or more.

[Preferred Composition of Animal Cell Cryopreservation Solution]

In a preferred embodiment, the animal cell cryopreservation solution may contain 25 mM of DMGA-PLL as a polymer (polyampholyte), and, for example, 0.5 M or more of sucrose, 6M or more of EG, and 10% by weight or more of epichlorohydrin-crosslinked sucrose polymer macromolecule, such as 0.75 M or more of sucrose, 5.5 M or more of EG (or 6 M or more of EG), and 10% by weight or more of epichlorohydrin-crosslinked sucrose polymer macromolecule.

In a preferred embodiment, the animal cell cryopreservation solution may contain 25 mM of COOH-PLL (SA-PLL) as a polymer (polyampholyte), and, for example, 0.5 M or more of sucrose, 6.5 M or more of EG, and 20% by weight or more of epichlorohydrin-crosslinked sucrose polymer macromolecule, such as 0.75 M or more of sucrose, 6 M or more of EG (or 6.5 M or more of EG), and 10% by weight or more (or 20% by weight or more) of epichlorohydrin-crosslinked sucrose polymer macromolecule.

[Method for Cryopreserving Animal Cells]

The method for cryopreserving animal cells according to the present invention can be carried out by a method including the steps of immersing the animal cells in the animal cell cryopreservation solution and freezing the animal cells in the animal cell cryopreservation solution by lowering a temperature.

In a preferred embodiment, after the step of freezing the animal cells by lowering the temperature, the method according to the present invention can involve a step of thawing the frozen animal cells in the animal cell cryopreservation solution by elevating a temperature.

[Temperature Lowering and Crystallization]

In order to prevent damage to the animal cells, it is preferable that the animal cells can be frozen while maintaining a vitreous state (an amorphous state) without generation of crystallization in the cryopreservation solution when lowering the temperature to freeze the animal cells. Although crystallization hardly occurs if the cooling rate is increased, the increase in the cooling rate will involve increased constraints on handling of the cells. Therefore, this will be a difficult alternative for three-dimensional cell structures, tissues, organs and the like which have larger heat capacity and uneven thermal conductivity, because of cracks due to the increased cooling rate, tissue destruction due to formation of cracks and the like. According to the present invention, the freezing in the vitreous state is possible without generation of crystallization, for example by selecting the cooling rate from ranges of from 5° C./min to 50° C./min, and from 10° C./min to 30° C./min. The presence or absence of generation of crystallization can be detected by DSC measurement as shown in Examples.

[Temperature Elevating and Recrystallization]

Even if the animal cells have been frozen in the vitreous state, the vitreous state may be broken and recrystallization of the cryopreservation solution may occur when the frozen animal cells are thawed by elevating the temperature. Therefore, it is preferable that the frozen animal cells can be thawed while preventing recrystallization, in order to prevent damage to the animal cells due to cryopreservation. Although recrystallization hardly occurs if the heating rate is increased, the increase in the heating rate will involve increased constraints on handling of the cells, as with the case of the cooling rate. Therefore, this will be a difficult alternative for three-dimensional cell structures, tissues, organs and the like which have larger heat capacity and uneven thermal conductivity, because of cracks due to the increased heating rate, tissue destruction due to formation of cracks and the like. According to the present invention, the animal cells can be thawed while maintaining the vitreous state without generation of recrystallization, for example by selecting the heating rate from ranges of from 5° C./min to 100° C./min, from 5° C./min to 50° C./min and from 10° C./min to 50° C./min. The presence or absence of generation of recrystallization can be detected by DSC measurement as shown in Examples.

[Vitrification Ability]

The vitrification ability as used herein refers to the ability to maintain the vitreous state to prevent recrystallization, which may be, for example, the ability to prevent crystallization during the temperature lowering and/or the ability to prevent recrystallization during the temperature elevating. The improved vitrification ability can be achieved as long as the ability is sufficient during either the temperature lowering or the temperature elevating. By using the animal cell cryopreservation solution having the improved vitrification ability, good cryopreservation can be achieved even for the three-dimensional cell structures, tissues, organs and the like which have larger heat capacity and uneven thermal conductivity. Therefore, the animal cell cryopreservation solution according to the present invention is suitable for use in the animal cells in the form of a three dimensional cell structure, tissue, organ or the like. According to the animal cell cryopreservation solution of the present invention, the animal cells can be frozen, preserved and thawed with higher viability.

[Cryopreservation]

Generally, in the case of the vitrifying method involving rapidly dipping in liquid nitrogen, the vitreous state once achieved can be semipermanently maintained at the liquid nitrogen temperature which is equal to or lower than the glass transition point of water (generally around −130° C.). However, when left to stand in an electric freezer at a higher temperature, from a thermodynamic view point, crystallization eventually occur so that ice crystals are formed. Therefore, there has been a need for allowing excellent vitreous state to be maintained, such as allowing cryopreservation under a higher temperature, in order to achieve cryopreservation by utilizing a highly convenient electric freezer. According to the animal cell cryopreservation solution of the present invention, the vitreous state is extremely stably maintained, so that even by cryopreservation at a higher preservation temperature (for example, preserved at −80° C. for 1 day in Examples), high cell viability can be maintained. It goes without saying that a lower temperature is preferable for maintaining the vitreous state, but according to the present invention, the temperature to be preserved after freezing may be, for example, −100° C. or less, −130° C. or less, or for example, from −196 to −80° C., from −130° C. to −100° C., and the number of days to be preserved may be, for example, 2 hours or more, 6 hours or more, 0.5 days or more, 1 day or more, or 1 day to 10 years or more.

[Glass Transition Point]

The animal cell cryopreservation solution according to the present invention achieves a glass transition point lower than that of the prior art by containing the vitreous state stabilizing agent for the animal cell cryopreservation solution as described above. In a preferred embodiment, the glass transition temperature of the animal cell cryopreservation solution may be, for example, from −135° C. to −100° C., from −135° C. to −80° C., or from −120° C. to −115° C.

EXAMPLES

Hereinafter, the present invention will be described in detail with reference to Examples. However, the present invention is not limited to Examples illustrated below. It should be noted that in Examples, "%" and "parts" represent % by weight and parts by weight, respectively, unless otherwise specified.

[Synthesis of COOH-PLL]

Figure 23:
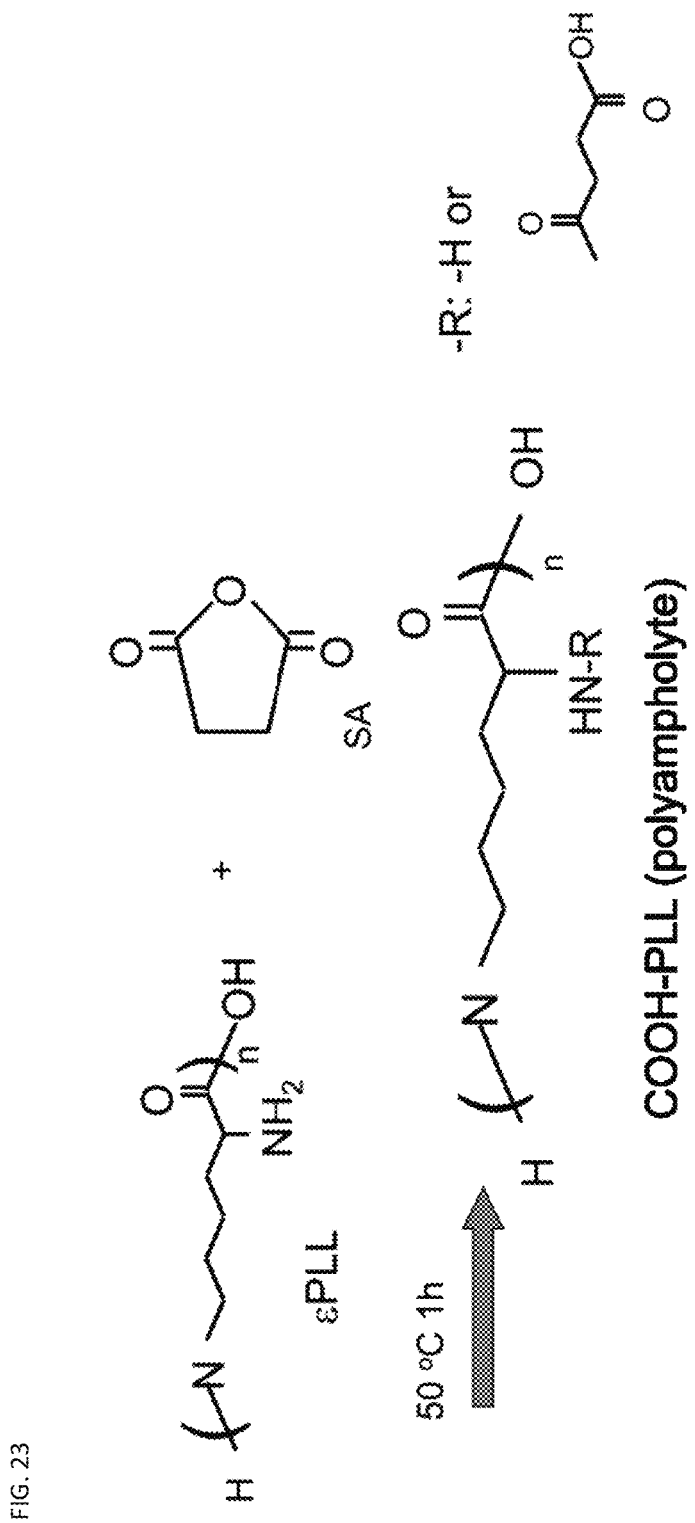
FIG. 23 is a drawing illustrating the reaction formula for synthesis of COOH-PLL.

Succinic anhydride (SA, TOKYO CHEMICAL INDUSTRY CO., LTD.) was added to ε-poly-L-lysine (25% aqueous solution, JNC, an average molecular weight of 4000) such that an amount of the former was from 15 to 50 mol % (or from 15 to 65 mol %) relative to the amino groups of the latter, and allowed to react at 50° C. for 1 hour to prepare a carboxylated polylysine (COOH-PLL). It should be noted that when used at a concentration of 10% by weight in terms of the amount of ε-poly-L-lysine (PLL) which is the starting material, the concentration corresponds to 25 mM based on the value of the average molecular weight of PLL of 4000, and so, for example, in the case of 10% by weight in terms of PLL, hereinafter, the concentration of COOH-PLL may be shown as 25 mM. Hereinafter, the carboxylated polylysine may be referred to as SA-PLL or COOH-PLL. The amount of the carboxyl groups introduced into COOH-PLL is 65% relative to the amino groups in the side chains of ε-poly-L-lysine, which may be referred to as PLL(0.65) or SA(65)-PLL, unless otherwise noted. The reaction scheme for synthesis of the COOH-PLL is shown in FIG. 23.

[Synthesis of BSA-PLL]

Butylsuccinic anhydride (BSA, TOKYO CHEMICAL INDUSTRY CO., LTD.) was added to ε-poly-L-lysine (25% aqueous solution, JNC, an average molecular weight of 4000) such that an amount of the former was from 15 to 50 mol % (or from 15 to 65 mol %) relative to the amino groups of the latter, and allowed to react at 50° C. for 1 hour to prepare a butylcarboxylated polylysine (BSA-PLL). It should be noted that when used at a concentration of 10% by weight in terms of the amount of ε-poly-L-lysine (PLL) which is the starting material, the concentration corresponds to 25 mM based on the value of the average molecular weight of PLL of 4000, and so, for example, in the case of 10% by weight in terms of PLL, hereinafter, the concentration of BSA-PLL may be shown as 25 mM. The reaction scheme for synthesis of the BSA-PLL is shown below. In the scheme, the upper stage represents reactants and the lower stage represents a product.

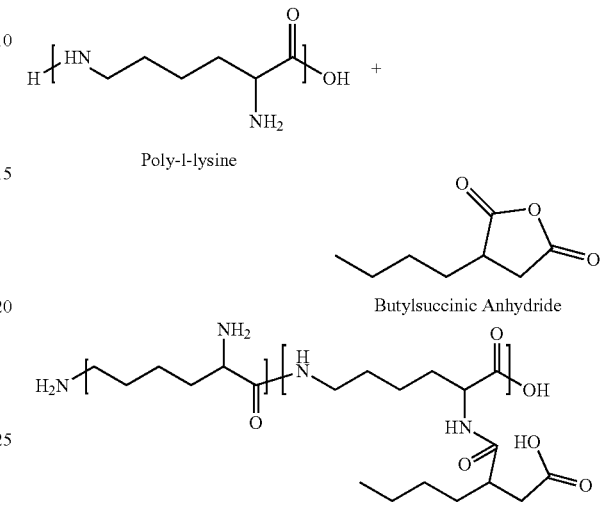

[Synthesis of BSA-SA-PLL]

The amino groups of ε-poly-L-lysine (25% aqueous solution, JNC, an average molecular weight of 4000) was carboxylated with butylsuccinic anhydride as stated above, and further carboxylated with succinic anhydride (SA) to prepare a butylcarboxylated-carboxylated-polylysine (BSA-SA-PLL). The numbers within the parentheses in the abbreviations as described below indicate the incorporated rates of the respective carboxyl groups to the amino groups of polylysine. For example, BSA(35)-SA(30)-PLL refers to a polyampholyte resulting from reaction of 35% of the amino groups with BSA and 30% of the amino groups with SA, among the amino groups of polylysine. In this case, the total amount of incorporated carboxyl groups is 65%. Additionally, BSA(15)-SA(50)-PLL and BSA(50)-SA(15)-PLL were also synthesized. It should be noted that the simple expression "BSA-PLL" means BSA(50)-PLL in which 50% of the amino groups of PLL was substituted with BSA and PLL did not react with SA. It also should be noted that when used at a concentration of 10% by weight in terms of the amount of ε-poly-L-lysine (PLL) which is the starting material, the concentration corresponds to 25 mM based on the value of the average molecular weight of PLL of 4000, and so, for example, in the case of 10% by weight in terms of PLL, hereinafter, the concentration of BSA-SA-PLL may be shown as 25 mM.

[Synthesis of DMGA-PLL]

3,3-dimethylglutaric anhydride (DMGA, Sigma Aldrich) was added to ε-poly-L-lysine (25% aqueous solution, JNC, an average molecular weight of 4000) such that an amount of the former was from 15 to 50 mol % (or from 15 to 65 mol %) relative to the amino groups of the latter, and allowed to react at 50° C. for 1 hour to prepare a dimethyl glutar carboxylated polylysine (DMGA-PLL) (3,3-dimethyl glutarated polylysine anhydride). It should be noted that when used at a concentration of 10% by weight in terms of the amount of ε-poly-L-lysine (PLL) which is the starting material, the concentration corresponds to 25 mM based on the value of the average molecular weight of PLL of 4000, and so, for example, in the case of 10% by weight in terms of PLL, hereinafter, the concentration of DMGA-PLL may be shown as 25 mM. The structural formula of 3,3-dimethylglutaric anhydride (DMGA) is shown below. (The reaction scheme for synthesis of the DMGA-PLL is shown below. Those skilled in the art will understand that the two kinds of repeating units in the structural formula of DMGA-PLL do not necessarily appear regularly or periodically as a result of the modification reaction with DMGA in the chains of ε-poly-L-lysine, and ordinarily define only the proportion of the units present in the chains of the polymer. That is, the repeating values X and Y mean a molar fraction of each partial structure in the molecule. A ratio of Y/(X+Y) is the content rate of repeating units modified with DMGA, and may be, for example in a range of from 0.5 to 0.70, or from 0.5 to 0.65.)

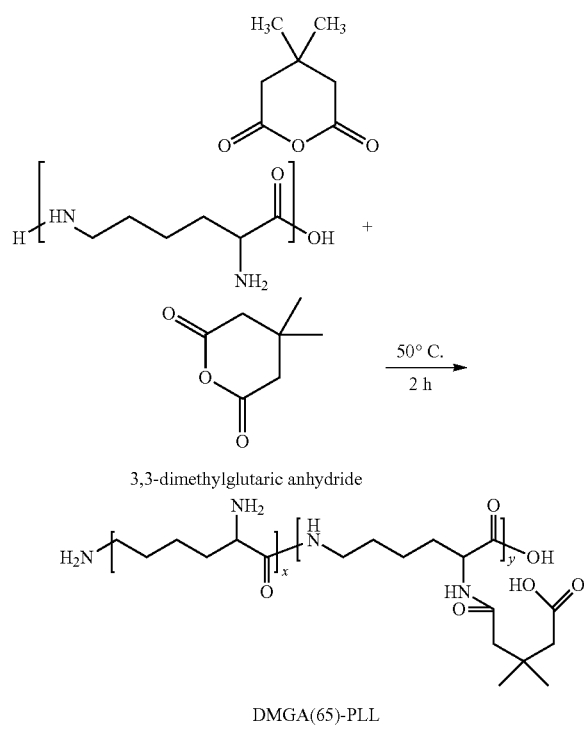

[Preparation of Vitrifying Solution]

Each vitrifying solution was prepared by providing a mixed solution of ethylene glycol (EG) and sucrose (a phosphate buffer PBS solution) as a base solution and adjusting a final concentration of each carboxylated polylysine therein to 12.5 mM. The concentration of sucrose was fixed at 0.5 M and the concentration of EG was varied from 4M to 6.5 M.

[DSC Measurement]

Each vitrifying solution was evaluated by a differential scanning calorimeter (DSC) (product name DSC 6200 available from Seiko Instruments Inc.) as follows.

10 μL of each vitrifying solution was placed on an aluminum pan for DSC, and the temperature was lowered to −120° C. at a cooling rate of 10° C./min by means of liquid nitrogen, and the presence or absence of crystallization was confirmed from the presence or absence of a peak in a graph of the DSC measurement. The temperature was elevated from that temperature to room temperature at a heating rate of 10° C./min, and the presence or absence of recrystallization was confirmed from the presence or absence of a peak in a graph of the DSC measurement.

Reference Comparative Example 1

[Evaluation of Recrystallization of Conventional Vitrifying Solution by DSC]

Once the conventional vitrifying solutions were frozen with liquid nitrogen, their characteristics were evaluated by the DSC measurement procedures as stated above, with the exception that the heating rate was 50° C./min. The conventional vitrifying solutions used are as follows. The results of the DSC measurement are shown in FIG. 1.

DAP213: an aqueous solution containing 2 M of DMSO, 1 M of acetamide, and 3 M of propylene glycol;

EG6.5M-Suc0.75M: an aqueous solution containing 6.5 M of ethylene glycol and 0.75 M of sucrose;

EG6.5M-Suc0.75M-PLL(0.65)10%, an aqueous solution containing 6.5 M of ethylene glycol, 0.75 M of sucrose and 10% by weight of SA(65)-PLL.

FIG. 1 is a graph showing results of DSC measurement of the conventional vitrifying solutions at the heating rate of 50° C./min. For DAP, an exothermic peak indicating generation of recrystallization was observed. For EG6.5M-Suc0.75M, an exothermic peak indicating generation of recrystallization was observed as well. For convenience of confirmation in the graph, each of these exothermic peaks was enclosed with an ellipse. For the vitrifying solution to which PLL(0.65) was added, i.e., EG6.5M-Suc0.75M-PLL (0.65)10%, no exothermic peak indicating generation of recrystallization was observed.

Reference Example 1

[Crystallization Test of Vitrifying Solution by DSC]

Characteristics of crystallization of each vitrifying solution were evaluated by the DSC measurement procedures as stated above, with the exception that the cooling rate was 10° C./min and the heating rate was 10° C./min. The vitrifying solutions used are as follows. The results of DSC measurement are shown in FIG. 2a (COOH-PLL), FIG. 2b (BSA-PLL) and FIG. 2c (BSA(35)-SA(30)-PLL), respectively.

COOH-PLL: an aqueous solution containing 25 mM of SA(65)-PLL, 6 M of ethylene glycol and 0.5 M of sucrose;

BSA-PLL: an aqueous solution containing 25 mM of BSA(65)-PLL, 6 M of ethylene glycol and 0.5 M of sucrose;

BSA(35)-SA(30)-PLL: an aqueous solution containing 25 mM of BSA(35)-SA(30)-PLL, 6 M of ethylene glycol and 0.5 M of sucrose.

FIG. 2a is a graph showing the result of crystallization evaluation by DSC measurement of the vitrifying solution containing COOH-PLL. In the temperature lowering process (the upper half of the graph), a peak indicating crystallization was observed around −70° C. to −80° C. That is, crystallization was generated due to the temperature lowering.

FIG. 2b is a graph showing the result of crystallization evaluation by DSC measurement of the vitrifying solution containing BSA-PLL. No peak indicating crystallization was observed in the temperature lowering process (the upper half of the graph). That is, the vitreous state was obtained without generation of crystallization due to the temperature lowering.

FIG. 2c is a graph showing the result of crystallization evaluation by DSC measurement of the vitrifying solution containing BSA(35)-SA(30)-PLL. No peak indicating crystallization was observed in the temperature lowering process (the upper half of the graph). That is, the vitreous state was obtained without generation of crystallization due to the temperature lowering.

Reference Example 2

[Crystallization Test of Vitrifying Solution by DSC]

Characteristics of crystallization of each vitrifying solution were evaluated by the DSC measurement procedures as stated above, with the exception that the cooling rate was 10° C./min and the heating rate was 10° C./min. The vitrifying solutions used are as follows. These were vitrifying solutions in which the concentration of ethylene glycol in BSA-PLL of Reference Example 1 was decreased from 6 M to 5 M and 4.5 M, respectively. The results of DSC measurement are shown in FIG. 3a (BSA-PLL, EG5M) and FIG. 3b (BSA-PLL, EG4.5M), respectively.

BSA-PLL, EG5M: an aqueous solution containing 25 mM of BSA(65)-PLL, 5 M of ethylene glycol and 0.5 M of sucrose;

BSA-PLL, EG4.5M: an aqueous solution containing 25 mM of BSA(65)-PLL, 4.5 M of ethylene glycol and 0.5 M of sucrose.

FIG. 3a is a graph showing the result of crystallization evaluation by DSC measurement of the vitrifying solution containing BSA-PLL, EG5M. No peak indicating crystallization was observed in the temperature lowering process (the upper half of the graph). That is, the vitreous state was obtained without generation of crystallization due to the temperature lowering.

FIG. 3b is a graph showing the result of crystallization evaluation by DSC measurement of the vitrifying solution containing BSA-PLL, EG4.5M. In the temperature lowering process (the upper half of the graph), a peak indicating crystallization was observed.

Reference Example 3

[Crystallization Test of Vitrifying Solution by DSC] Characteristics of crystallization of each vitrifying solution were evaluated by the DSC measurement procedures as stated above, with the exception that the cooling rate was 10° C./min and the heating rate was 10° C./min. The vitrifying solution used is as follows. This was a vitrifying solution in which the concentration of ethylene glycol in BSA(35)-SA(30)-PLL of Reference Example 1 was decreased from 6 M to 5.5 M. The results of DSC measurement are shown in FIG. 4 (BSA(35)-SA(30)-PLL, EG5.5M).

BSA(35)-SA(30)-PLL: an aqueous solution containing 25 mM of BSA(35)-SA(30)-PLL, 5.5 M of ethylene glycol and 0.5 M of sucrose.

FIG. 4 is a graph showing the result of crystallization evaluation by DSC measurement of the vitrifying solution containing BSA(35)-SA(30)-PLL, EG5.5M. No peak indicating crystallization was observed in the temperature lowering process (the upper half of the graph). That is, the vitreous state was obtained without generation of crystallization due to the temperature lowering.

Reference Example 4

[Recrystallization Test of Vitrifying Solution by DSC]

Characteristics of crystallization of each vitrifying solution were evaluated by the DSC measurement procedures as stated above, with the exception that the cooling rate was 10° C./min and the heating rate was 40° C./min. The vitrifying solutions used are as follows. The results of DSC measurement are shown in FIG. 5a (COOH-PLL), FIG. 5b (BSA-PLL) and FIG. 5c (BSA(35)-SA(30)-PLL), respectively.

COOH-PLL: an aqueous solution containing 25 mM of SA(65)-PLL, 6.5 M of ethylene glycol and 0.5 M of sucrose;

BSA-PLL: an aqueous solution containing 25 mM of BSA(65)-PLL, 6 M of ethylene glycol and 0.5 M of sucrose;

BSA(35)-SA(30)-PLL: an aqueous solution containing 25 mM of BSA(35)-SA(30)-PLL, 6.5 M of ethylene glycol and 0.5 M of sucrose.

FIG. 5a is a graph showing the result of recrystallization evaluation by DSC measurement of the vitrifying solution containing COOH-PLL. In the temperature elevating process (the lower half of the graph), a peak indicating crystallization was observed around −50° C. to −20° C. That is, recrystallization was generated due to the temperature elevating.

FIG. 5b is a graph showing the result of recrystallization evaluation by DSC measurement of the vitrifying solution containing BSA-PLL. No peak indicating recrystallization was observed in the temperature elevating process (the lower half of the graph). That is, the vitreous state transferred to a liquid state without generation of recrystallization due to the temperature elevating.

FIG. 5c is a graph showing the result of recrystallization evaluation by DSC measurement of the vitrifying solution containing BSA(35)-SA(30)-PLL. No peak indicating recrystallization was observed in the temperature elevating process (the lower half of the graph). That is, the vitreous state transferred to a liquid state without generation of recrystallization due to the temperature elevating.

Reference Example 5

[Cell Viability Test]

Cytotoxicity of each vitrifying solution was evaluated by the following cell viability test.

MSCs (mesenchymal stem cells) (Riken BioResource Research Center) were cultured on a petri dish to prepare a cell sheet. The prepared cell sheet was then immersed in each vitrifying solution as described below at 0° C. for 20 minutes. The cell sheet was then stained with Tripan Blue and then observed by an inverted phase contrast microscope to measure viability.

The results obtained for the following vitrifying solutions are shown in FIG. 6a:

BSA-PLL: an aqueous solution containing 25 mM of BSA(65)-PLL, 5 M of ethylene glycol and 0.5 M of sucrose;

COOH-PLL: an aqueous solution containing 25 mM of SA(65)-PLL, 6.5 M of ethylene glycol and 0.5 M of sucrose;

Control: an aqueous solution containing 5 M of ethylene glycol and 0.5 M of sucrose.

The results obtained for the following vitrifying solutions are shown in FIG. 6b:

BSA-SA-PLL: an aqueous solution containing 25 mM of BSA(35)-SA(30)-PLL, 5.5 M of ethylene glycol and 0.5 M of sucrose;

COOH-PLL: an aqueous solution containing 25 mM of SA(65)-PLL, 6.5 M of ethylene glycol and 0.5 M of sucrose;

Control: an aqueous solution containing 5 M of ethylene glycol and 0.5 M of sucrose.

FIGS. 6a and 6b are graphs showing cell viability in each vitrifying solution. BSA-SA-PLL exhibited improved cell viability as compared with that of BSA-PLL and had a viability value higher than that of each of COOH-PLL and Control.

[Summary of Results of Reference Examples 1 to 5 and Reference Comparative Example 1]

For COOH-PLL in which 65% of the amino groups was carboxylated only with succinic anhydride, the concentration of EG required for suppressing crystallization in the temperature lowering process was 6.5 M, whereas for BSA-PLL, vitrification was possible even if the concentration of EG was decreased to 5 M. This demonstrated the improved vitrification ability of BSA-PLL.

When BSA(35)-SA(30)-PLL was used, vitrification could be observed even if the concentration of EG was decreased to 5.5 M. The lower concentration of BSA led to higher vitrification ability, but it tended to slightly decrease cell viability (slightly increase cytotoxicity). However, BSA (35)-SA(30)-PLL exhibited sufficient high cell viability.

In the temperature elevating process at the heating rate of 40° C./min, recrystallization was observed for COOH-PLL, whereas the peak of recrystallization disappeared for BSA-PLL. Thus, it was found that BSA-PLL also suppressed recrystallization, demonstrating the stability of the vitreous state.

Reference Example 6

[Crystallization Test of Vitrifying Solution by DSC]

Characteristics of crystallization of each vitrifying solution were evaluated by the DSC measurement procedures as stated above, with the exception that the cooling rate was 10° C./min and the heating rate was 10° C./min. The vitrifying solutions used are as follows. The results of DSC measurement are shown in FIG. 7a (DMGA-PLL, EG6M), FIG. 7b (DMGA-PLL, EG5M), FIG. 7c (DMGA-PLL, EG4.5 M) and FIG. 7d (DMGA-PLL, EG4M), respectively.

DMGA-PLL, EG6M: an aqueous solution containing 25 mM of DMGA(65)-PLL, 6 M of ethylene glycol and 0.5 M of sucrose;

DMGA-PLL, EG5M: an aqueous solution containing 25 mM of DMGA(65)-PLL, 5 M of ethylene glycol and 0.5 M of sucrose;

DMGA-PLL, EG4.5M: an aqueous solution containing 25 mM of DMGA(65)-PLL, 4.5 M of ethylene glycol and 0.5 M of sucrose;

DMGA-PLL, EG4M: an aqueous solution containing 25 mM of DMGA(65)-PLL, 4 M of ethylene glycol and 0.5 M of sucrose.

FIG. 7a is a graph showing the result of crystallization evaluation by DSC measurement of the vitrifying solution containing DMGA-PLL, EG6M. No peak indicating crystallization was observed in the temperature lowering process (the upper half of the graph). That is, the vitreous state was obtained without generation of crystallization due to the temperature lowering.

FIG. 7b is a graph showing the result of crystallization evaluation by DSC measurement of the vitrifying solution containing DMGA-PLL, EG5M. No peak indicating crystallization was observed in the temperature lowering process (the upper half of the graph). That is, the vitreous state was obtained without generation of crystallization due to the temperature lowering.

FIG. 7c is a graph showing the result of crystallization evaluation by DSC measurement of the vitrifying solution containing DMGA-PLL, EG4.5M. No peak indicating crystallization was observed in the temperature lowering process (the upper half of the graph). That is, the vitreous state was obtained without generation of crystallization due to the temperature lowering.

FIG. 7d is a graph showing the result of crystallization evaluation by DSC measurement of the vitrifying solution containing DMGA-PLL, EG4M. In the temperature lowering process (the upper half of the graph), a peak indicating crystallization was observed around −50° C. to −60° C.

Reference Example 7

As Reference Example 7, an experiment that will be described below was carried out. Other conditions were the same as those described in Reference Example 1, unless otherwise noted.

[Preparation of Vitrifying Solution]

Each vitrifying solution was prepared by providing a mixed solution of ethylene glycol (EG) and sucrose (PBS) as a base solution and adjusting a final concentration of each carboxylated polylysine therein to 25 mM. The concentration of sucrose (Su) was fixed at 0.5 M and the concentration of EG was varied from 4M to 6.5 M. The compositions of the vitrifying solutions used are as follows:

Control: 0.5 M of Su, 6.5 M of EG: FIG. 8;
25 mM of SA-PLL (COOH-PLL), 0.5 M of Su, 6.5 M of EG: FIG. 9;
25 mM of COOH-PLL, 0.5 M of Su, 5.5 M of EG: FIG. 10a;
25 mM of COOH-PLL, 0.5 M of Su, 5 M of EG: FIG. 10b;
25 mM of BSA-PLL, 0.5 M of Su, 5 M of EG: FIG. 11a;
25 mM of BSA-PLL, 0.5 M of Su, 4.5 M of EG: FIG. 11b;
25 mM of DMGA-PLL, 0.5 M of Su, 4.5 M of EG: FIG. 12a;
25 mM of DMGA-PLL, 0.5 M of Su, 4 M of EG: FIG. 12b;
25 mM of COOH-PLL, 0.5 M of Su, 6 M of EG: FIG. 13a;
25 mM of BSA-PLL, 0.5 M of Su, 6 M of EG: FIG. 13b;
25 mM of DMGA-PLL, 0.5 M of Su, 6 M of EG: FIG. 13c.

[DSC Measurement]

Each vitrifying solution was evaluated as follows:

10 μL of each vitrifying solution was placed on an aluminum pan for DSC, and the temperature was lowered to −170° C. at a cooling rate of 10° C./min by means of liquid nitrogen, and the presence or absence of crystallization and vitrification was confirmed. Further, the temperature was elevated from that temperature to room temperature at a heating rate of 10° C./min, and the presence or absence of recrystallization was confirmed.

FIG. 8 shows a DSC curve when the temperature of a solution containing 6.5 M of EG and 0.5 M sucrose with no polyampholyte as a vitrifying solution was lowered and elevated at 10° C./min, and FIG. 9 shows a DSC curve when the temperature of a solution containing 25 mM of COOH-PLL, 6.5 M of EG and 0.5 M of sucrose as a vitrifying solution was lowered and elevated at 10° C./min. Referring to FIG. 8, when no polyampholyte was present, a peak of crystallization was observed at around −90° C. and a peak of melting was observed at around −30° C. On the other hand, when COOH-PLL was added, no peak of crystallization was observed, and a glass transition point was observed around −130° C., indicating that the solution was vitrified. Further, during the temperature elevating, a peak of recrystallization was also observed around −60° C.

FIGS. 10a and 10b show the results when the EG concentrations of the COOH-PLL-added vitrifying solution were decreased to 5.5 M and 5.0 M. Vitrification was observed at the concentration of 5.5 M, whereas a crystallization peak was observed at the concentration of 5 M. It was found that the effect of suppressing crystallization by COOH-PLL was exerted at the concentration of EG of 5.5 M or more.

On the one hand, it was found from FIGS. 11a and 11b that the EG concentration which could suppress crystallization by BSA-PLL was 5 M. It was found from FIGS. 12a and 12b that the EG concentration which could suppress crystallization by DMGA-PLL was 4.5 M. It was confirmed that the effect of suppressing crystallization by BSA-PLL was exerted at the concentration of EG of 5 M or more. On the other hand, it was found that the effect of suppressing crystallization by DMGA-PLL was exerted at the concentration of EG of 4.5 M or more. These results demonstrated that among the synthesized and compared polyampholytes, DMGA-PLL had the highest effect of suppressing crystallization.

FIGS. 13a, 13b, and 13c show DSC results of solutions containing three polyampholytes, 6.0 M of EG and 0.5 M of sucrose. It was found that for all the polyampholytes, crystallization was not generated and vitrification was generated at this concentration of EG. On the other hand, as can be seen from FIGS. 13a and 13b, recrystallization was observed during the temperature elevating for COOH-PLL and BSA-PLL, whereas as can be seen from FIG. 13c, no recrystallization was observed for DMGA-PLL. These results demonstrated that DMGA-PLL had higher effects of suppressing crystallization and recrystallization than those of the other polyampholytes.

Reference Example 8

[Cell Viability Test]

Figure 24:
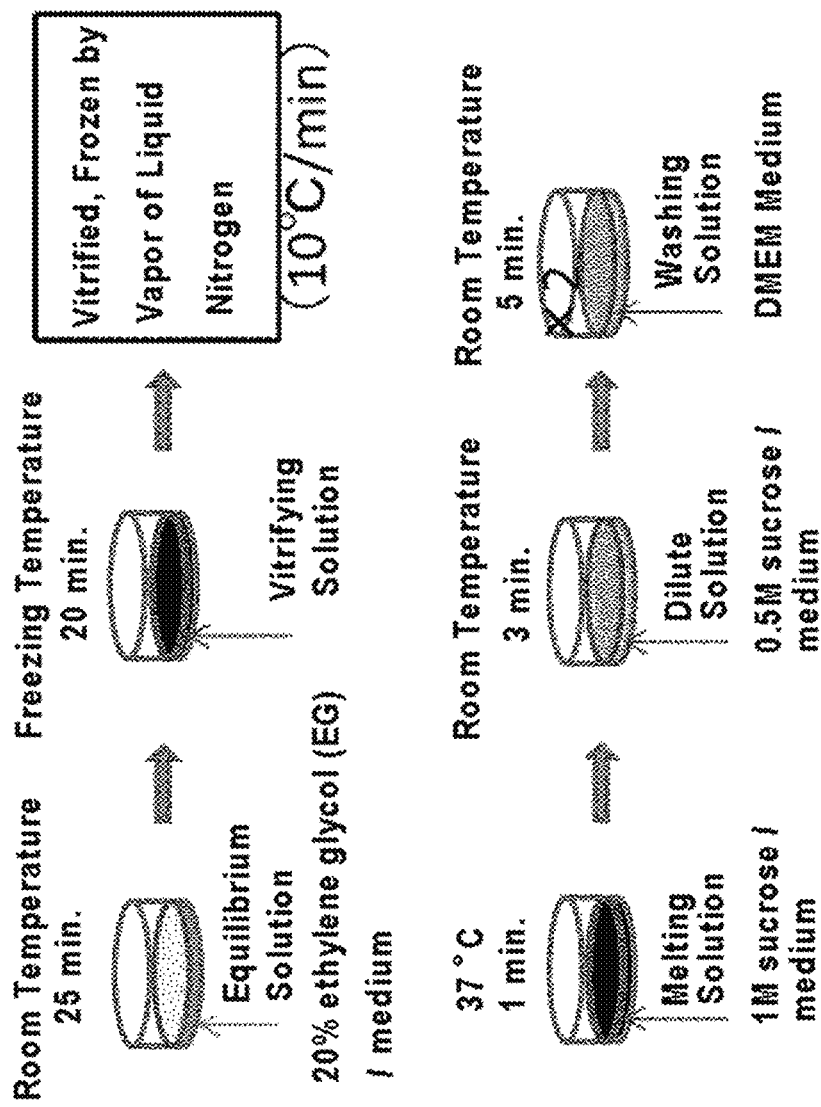
FIG. 24 is an explanatory diagram showing an outline of the procedures of Reference Example 8.

Next, a sheet of human mesenchymal stem cells (MSCs) (Riken BioResource Research Center) was vitrified and preserved in the vitrifying solutions using those polyampholytes, and an experiment for confirming cell viability was carried out by the following procedures. An explanation showing the outline of the procedures of this experiment is shown in FIG. 24. Compositions of the vitrifying solutions used are as follows:
Control: 6 M of EG, 0.5 M of Su: FIG. 14a;
COOH-PLL: 25 mM of COOH-PLL, 6 M of EG, 0.5 M of Su: FIG. 14b;
BSA-PLL: 25 mM of BSA-PLL, 6 M of EG, 0.5 M of Su: FIG. 14c;
DMGA-PLL: 25 mM of DMGA-PLL, 6 M of EG, 0.5 M of Su: FIG. 14d;
Control: 6 M of EG, 0.5 M of Su: a in FIG. 15;
COOH-PLL: 25 mM of COOH-PLL, 6 M of EG, 0.5 M of Su: b in FIG. 15;
BSA-PLL: 25 mM of BSA-PLL, 6 M of EG, 0.5 M of Su: c in FIG. 15;
DMGA-PLL: 25 mM of DMGA-PLL, 6 M of EG, 0.5 M of Su: d in FIG. 15.

MSCs were cultured using Dulbecco's Modified Eagle's Medium (DMEM) supplemented with 10% fetal bovine serum in an incubator at 37° C. After being in a confluent state on a 3.5 cm cell culture dish (IWAKI), the cells were continuously cultured for one week to obtain an MSC sheet which was used for the experiment.

After the culture solution was removed, 2 mL of a 20% EG/DMEM solution was added to the MSC sheet, and left to stand at room temperature for 25 minutes to equilibrate it. After removing the solution, 500 µL of each vitrifying solution was then added at a freezing temperature and left to stand for 20 minutes. Subsequently, the culture dish was maintained at a position of 1 cm from a vapor of liquid nitrogen to freeze it. It has been known that a freezing rate can be controlled by the distance from the vapor of liquid nitrogen at this time, and that a freezing rate of about 10° C./min can be obtained at the position of 1 cm from the vapor. The culture dish was then allowed to stand in a steam atmosphere for 10 minutes and sufficiently solidified, and then immersed in liquid nitrogen to complete the freezing. Subsequently, thawing operation was carried out. The thawing was carried out by adding 3 ml of a 1 M sucrose/DMEM solution warmed to 37° C. to the MSC sheet culture dish taken out from liquid nitrogen and removing the solution after one minute. Then, 3 mL of a 0.5 M sucrose/DMEM solution was added and removed after 3 minutes. Subsequently, 3 mL of DMEM was added, removal was repeated twice after 5 minutes, and finally 2 mL of DMEM was added and culturing was carried out in an incubator at 37° C. On the next day, cell viability was evaluated by a Live/Dead assay.

The results of this experiment are shown in FIGS. 14a, 14b, 14c and 14d. FIGS. 14a to 14d are fluorescent microscopy photographs of double-stained cell sheets frozen and thawed by the above procedures using the respective vitrifying solutions, and each bar at the lower right of the visual field shows 100 µm. By the Live/Dead assay, living cells were stained in green color with Calsein AM and dead cells were stained in red color with an ethidium homodimer. Viability was determined by counting the number of living cells (green-stained cells) and dead cells (red-stained cells) in the visual fields in FIGS. 14a, 14b, 14c and 14d, respectively. The vitrifying solution with no polyampholyte (FIG. 14a) exhibited viability of about 30%, whereas the COOH-PLL system (FIG. 14b) exhibited viability of about 75%, the BSA-PLL system (FIG. 14c) exhibited viability of about 55%, and the DMGA-PLL system (FIG. 14d) exhibited viability of about 93%. Bar graphs were created from these values, which are shown in FIG. 15. The horizontal axes a, b, c, and d in FIG. 15 correspond to a, b, c, and d in FIG. 14, respectively. The results demonstrated an outstanding effect of DMGA-PLL.

Example 1, Comparative Examples 1 to 3

[Improvement of Glass Transition Point]

In general, the glass transition point of water is around −130° C. In the case of the vitrifying method involving rapidly immersing in liquid nitrogen, the vitreous state once achieved can be semipermanently maintained at the liquid nitrogen temperature. This is because the liquid nitrogen temperature is equal to or lower than the glass transition point of water. On the other hand, when water in a vitreous state is allowed to stand in a freezer at −80° C. or the like, crystallization, in principle, will eventually occur thermodynamically, and ice crystals will be formed. Therefore, in order to allow vitrified preservation in a freezer, it is desirable to increase the glass transition point of water to a temperature equal to or higher than that of the freezer. To this end, investigations of the optimum composition of the vitrifying solutions, such as adding of solutes such as ethylene glycol and sucrose at high concentration, were conducted.

More particularly, as Comparative Examples 1 to 3, three vitrifying solutions: DAP 213, EG 6.5 M/sucrose 0.5 M, and EG 6.5 M/sucrose 0.5 M/COOH-PLL 25 mM, were prepared and subjected to DSC measurement to determine the glass transition points. 10 μL of each solution was placed in an aluminum pan and once vitrified by immersing the solution in liquid nitrogen. This was set to DSC (TA Instruments, Discovery DSC) in which a sample chamber was cooled to −170° C. in advance, and the temperature was elevated at 10° C./min and the glass transition point was determined.

FIG. 16 is a graph showing recrystallization behavior of various vitrifying solutions. As shown in FIG. 16, the glass transition points were −126° C. for DAP and −123° C. for the solution of EG 6.5 M/sucrose 0.5 M, whereas the glass transition point could be increased to −119° C. for the solution to which the COOH-PLL type vitrifying solution was added.

Next, as Example 1, the same test was conducted by adding 10% sucrose polymer macromolecule (product name: Ficoll; an average molecular weight of 70,000; manufactured by GE Health Sciences) as a hydrophilic polysaccharide. As a result, it was possible to increase the Tg to −113° C., as shown in FIG. 17. Commercial electric freezers that are easily available include those at −110° C. and −130° C., and the results demonstrate that the Tg are close to a range that can be vitrified and preserved in the freezer at −110° C. FIG. 17 is a graph showing recrystallization behavior of the DMGA-PLL vitrifying solution (DMGA-PLL 25 mM, Su 0.5 M, EG 6.0 M, Ficoll 10%).

[Vitrification Evaluation Test]

The presence or absence of crystallization when each vitrifying solution is left to stand in a freezer at −80° C. for 3 hours is shown in FIGS. 18 and 19.

FIG. 18 is a photograph showing appearance of a 96-well plate after injecting into each well 50 μL of a vitrifying solution obtained by adding 25 mM of DMGA-PLL or COOH-PLL (SA-PLL) to a solution of EG 6 M, sucrose 0.5 M and Ficoll 10%, and then leaving the vitrifying solution to stand at −80° C. for 3 hours. The wells with added COOH-PLL became white and opaque, indicating that crystallization occurred (the wells in the seventh and eighth columns from the left in FIG. 18). In contrast, all the wells with no added DMGA-PLL remained transparent, indicating that these wells generated no crystallization and were in the vitreous state (the wells in the first and second columns from the left in FIG. 18).

FIG. 19 is a photograph showing appearance of a 96-well plate after injecting into each well 50 μL of each of vitrifying solutions obtained by respectively adding polysaccharides to a solution of EG 6 M, sucrose 0.5 M and DMGA 25 mM, and then leaving the vitrifying solutions to stand at −80° C. for 3 hours. The numbers (1) to (4) labelled in the photograph indicate that each of solutions having the following compositions was injected into three wells:

(1) EG 6 M, sucrose 0.5 M;
(2) EG 6 M, sucrose 0.5 M, DMGA 25 mM;
(3) EG 6 M, sucrose 0.5 M, DMGA 25 mM, Ficoll 10%; and
(4) EG 6 M, sucrose 0.5 M, DMGA 25 mM, pullulan 10%.

In FIG. 19, only the case where Ficoll was added (the above (3)) maintained complete transparency and was in the vitreous state. In the DMGA-free, polysaccharide-free and pullulan-added systems, all the systems became white and opaque, and crystallization was observed (the above (1), (2), and (4)).

The experimental system shown in FIG. 19 was performed with various varying concentrations of EG and sucrose, and the results are summarized in Table 1. Table 1 shows the vitrification evaluation of each vitrifying solution after leaving it to stand at −80° C. for 3 hours. 25 mM of DMGA-PLL or COOH-PLL was added as a polymer, or no polymer was added. Ficoll or pullulan was added as a hydrophilic polysaccharide, or no hydrophilic polysaccharide was added. Evaluation of vitrification was conducted by visual observation. In the case where all wells of the relevant sample were transparent, the sample was considered to be always vitrified, and labelled as "0" (circle). In the case where all wells of the relevant sample became white and opaque, the sample was considered to be always crystallized, and labelled as x (crossed). In the case where one parts of wells of the relevant sample were transparent and other parts were white and opaque, the sample was determined to be both vitrified and crystallized, and labelled as A (triangle). As can be seen from Table 1, as the concentration of EG was higher, the vitreous state tended to be maintained, DMGA was more effective than COOH-PLL, and the effect of Ficoll was also significant.

TABLE 1

| DMGA-PLL (mM) | COOH-PLL (mM) | Su (M) | EG (M) | Ficoll (%) | Pullulan (%) | Vitrification Evaluation |
|---|---|---|---|---|---|---|
| 25 | 0 | 0.5 | 6 | 0 | 0 | x |
| 25 | 0 | 0.5 | 6 | 10 | 0 | ○ |
| 25 | 0 | 0.5 | 6.5 | 10 | 0 | ○ |
| 25 | 0 | 0.75 | 5.5 | 10 | 0 | Δ |
| 25 | 0 | 0.75 | 6 | 10 | 0 | ○ |
| 25 | 0 | 0.75 | 6.5 | 20 | 0 | ○ |
| 25 | 0 | 0.75 | 6 | 20 | 0 | ○ |
| 25 | 0 | 0.5 | 6 | 0 | 10 | x |
| 25 | 0 | 0 | 0 | 0 | 0 | x |
| 0 | 0 | 0.75 | 6.5 | 20 | 0 | x |
| 0 | 0 | 0.5 | 6 | 10 | 0 | x |
| 0 | 25 | 0.5 | 6 | 0 | 0 | x |
| 0 | 25 | 0.5 | 6.5 | 20 | 0 | Δ |
| 0 | 25 | 0.75 | 6 | 10 | 0 | Δ |
| 0 | 25 | 0.75 | 6.5 | 20 | 0 | ○ |

[Cell Preservation Test]

Next, an experiment was conducted to preserve a sheet of human mesenchymal stem cells (MSCs) (Riken BioResource Research Center) by vitrification.

The MSCs were cultured in an incubator at 37° C. using Dulbecco's Modified Eagle's Medium (DMEM) supplemented with 10% fetal bovine serum. A cell sheet continuously cultured for one week after being confluent in a 3.5 cm cell culture dish (IWAKI) was used for the experiment.

After the culture solution was removed, 2 mL of a 20% EG/DMEM solution was added to the MSC sheet, and left to stand at room temperature for 25 minutes to equilibrate it. Then, after removing the solution, 500 μL of each vitrifying solution was added at ice temperature, and left to stand for 20 minutes. The petri dish was then maintained at a position of 1 cm from a vapor of liquid nitrogen to freeze it. It is known that the freezing rate can be controlled by the distance from the liquid nitrogen vapor herein, and that a freezing rate of about 10° C./min can be obtained at a position of 1 cm from the vapor. The petri dish was then left to stand in a steam atmosphere for 10 minutes, sufficiently solidified and then immersed in the liquid nitrogen to complete the freezing. A thawing operation was then carried out. The thawing was carried out by adding 3 ml of 1 M sucrose/DMEM warmed to 37° C. to the MSC sheet culture dish taken out from the liquid nitrogen and removing the solution after 1 minute. 3 mL of a 0.5 M sucrose/DMEM solution was added and removed after 3 minutes. Subsequently, 3 mL of DMEM was added, removal was repeated twice after 5 minutes, and finally 2 mL of DMEM was added and transferred to incubation in an incubator at 37° C. On the next day, cell viability was evaluated by a Live/Dead assay. In double-stained fluorescence micrographs, green cells stained with Calsein AM are living cells and red cells stained with ethidium homodimer are dead cells.

FIGS. 20a, 20b, 20c and 20d are fluorescence microscopy photographs of the MSC sheets which were left to stand in a freezer at −80° C. for 1 hour with the vitrifying solutions having the respective compositions, then thawed and washed and double-stained on the next day. There are many black parts in the photographs, because peeling of cells occurred, but clearly there are many green living cells in the presence of COOH-PLL and DMGA-PLL. The compositions of the vitrifying solutions used are as follows:

EG 6 M, Su 0.5 M: FIG. 20a;
COOH-PLL 25 mM, EG 6 M, Su 0.5 M: FIG. 20b;
DMGA-PLL 25 mM, EG 6 M, Su 0.5 M: FIG. 20c; and
DMGA-PLL 25 mM, EG 6 M, Su 0.5 M, Ficoll 10%: FIG. 20d.

FIGS. 21a, 21b, 21c and 21d are fluorescence microscopy photographs of the MSC sheets which were left to stand in a freezer at −80° C. for 1 day with the vitrifying solutions having the respective compositions, then thawed and washed and double-stained on the next day. In this case, the combination of DMGA-PLL and Ficoll resulted in a significant increase in the number of green cells. The compositions of the vitrifying solutions used are as follows:

EG 6 M, Su 0.5 M: FIG. 21a;
COOH-PLL 25 mM, EG 6 M, Su 0.5 M: FIG. 21b;
DMGA-PLL 25 mM, EG 6 M, Su 0.5 M: FIG. 21c; and
DMGA-PLL 25 mM, EG 6 M, Su 0.5 M, Ficoll 10%: FIG. 21d.

As these quantitative results, Table 2 shows viability of MSCs after leaving them to stand at −80° C. in each vitrifying solution. As shown in Table 2, the results show the same tendency as in Table 1. In the vitrifying solution of EG 6 M, DMGA-PLL 25 mM, sucrose 0.5 M and Ficoll 10%, a measurable vitreous state could be maintained even at −80° C. and viability of the cells could be increased. This indicates that a cell structure for regenerative medicine, including the MSC sheet, can be cryopreserved by a commercially available high performance electric freezer at −130° C. or the like, without cryopreservation with the liquid nitrogen.

TABLE 2

| Vitrifying Solution | Viability after 1 h in −80° C./% | Viability after 1 day in −80° C./% |
| --- | --- | --- |
| EG6M, Suc 0.5M | 1.5 ± 2.1 | 0.05 ± 0.01 |
| SA-PLL 25 mM, EG6M, Suc 0.5M | 43.1 ± 16.7 | 31.4 ± 16.2 |
| DMGA-PLL 25 mM, EG6M, Suc 0.5M | 48.2 ± 22.3 | 21.1 ± 5.35 |

TABLE 2-continued

| Vitrifying Solution | Viability after 1 h in −80° C./% | Viability after 1 day in −80° C./% |
| --- | --- | --- |
| DMGA-PLL 25 mM, EG6M, Suc 0.5M, Ficoll 10% | 69.6 ± 11.1 | 47.8 ± 13.6 |

INDUSTRIAL APPLICABILITY

According to the present invention, an animal cell cryopreservation solution having an improved vitrification ability can be obtained. The present invention is an industrially useful invention.

What is claimed is:

1. A vitreous state stabilizing agent for an animal cell cryopreservation solution, comprising:
    at least one polyampholyte having amino groups and carboxyl groups in the same molecule; and
    at least one epichlorohydrin-crosslinked sucrose polymer macromolecule,
    wherein the polyampholyte is at least one carboxylated polyampholyte resulting from reaction of ε-poly-L-lysine with a compound represented by the following formula (II):

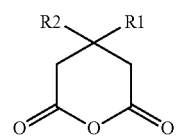

Formula (II)

in which:
R1 and R2 each represent a methyl group,
    wherein the at least one polyampholyte has a percentage of carboxylated amino groups among the amino groups in the side chains of ε-poly-L-lysine of 65%,
    wherein the epichlorohydrin-crosslinked sucrose polymer macromolecule has a molecular weight of 70,000, and
    wherein the animal cell cryopreservation solution comprises:
        10% by weight of the polyampholyte; and
        10% to 12.5% by weight of the epichlorohydrin-crosslinked sucrose polymer macromolecule.

2. An animal cell cryopreservation solution comprising a physiological solution, the physiological solution containing the vitreous state stabilizing agent for the animal cell cryopreservation solution according to claim 1.

3. The animal cell cryopreservation solution according to claim 2, wherein the animal cell cryopreservation solution has a glass transition point of from −135° C. to −80° C.

4. An animal cell cryopreservation solution comprising a physiological solution, the physiological solution containing:
    the vitreous state stabilizing agent for the animal cell cryopreservation solution according to claim 1; and
    ethylene glycol or propylene glycol at a concentration of from 3 to 8 M.

5. The animal cell cryopreservation solution according to claim 4, further containing sucrose at a concentration of from 0.1 to 1 M.

6. A method for cryopreserving animal cells, comprising the steps of:

immersing the animal cells in the animal cell cryopreservation solution according to claim 2; and freezing the animal cells in the animal cell cryopreservation solution by lowering a temperature.

7. The method for cryopreserving the animal cells according to claim 6, further comprising, after the step of freezing the animal cells in the animal cell cryopreservation solution by lowering the temperature, a step of thawing the frozen animal cells in the animal cell cryopreservation solution by elevating a temperature.

8. The method for cryopreserving the animal cells according to claim 6, wherein the step of freezing the animal cells in the animal cell cryopreservation solution by lowering the temperature comprises freezing the animal cells in a vitreous state by lowering the temperature.

9. The method for cryopreserving the animal cells according to claim 7, wherein the step of thawing the frozen animal cells in the animal cell cryopreservation solution by elevating the temperature comprises thawing the animal cells by elevating the temperature without recrystallization.

10. The method for cryopreserving the animal cells according to claim 6, wherein the step of freezing the animal cells in the animal cell cryopreservation solution by lowering the temperature comprises freezing the animal cells by lowering the temperature at a cooling rate of from 5° C./min to 50° C./min.

11. The method for cryopreserving the animal cells according to claim 7, wherein the step of thawing the frozen animal cells in the animal cell cryopreservation solution by elevating the temperature comprises thawing the frozen animal cells by elevating the temperature at a heating rate of from 5° C./min to 100° C./min.

12. The method for cryopreserving the animal cells according to claim 7, wherein the method comprises, after the step of freezing the animal cells in the animal cell cryopreservation solution by lowering the temperature and before the step of thawing the frozen animal cells in the animal cell cryopreservation solution by elevating the temperature, a step of preserving the frozen animal cells in the animal cell cryopreservation solution at a temperature of from −196° C. to −75° C.

* * * * *